(12) United States Patent
Raemaekers et al.

(10) Patent No.: US 8,865,668 B2
(45) Date of Patent: Oct. 21, 2014

(54) METHODS AND COMPOSITIONS FOR INCREASING RNA INTERFERENCE

(75) Inventors: Romaan Raemaekers, De Pinte (BE); Annelies Philips, Oostakker (BE)

(73) Assignee: Devgen N.V. (BE)

( * ) Notice: Subject to any disclaimer, the term of this patent is extended or adjusted under 35 U.S.C. 154(b) by 562 days.

(21) Appl. No.: 12/389,635

(22) Filed: Feb. 20, 2009

(65) Prior Publication Data

US 2009/0238805 A1    Sep. 24, 2009

Related U.S. Application Data

(60) Provisional application No. 61/030,029, filed on Feb. 20, 2008, provisional application No. 61/087,315, filed on Aug. 8, 2008, provisional application No. 61/118,105, filed on Nov. 26, 2008.

(51) Int. Cl.
*A61K 48/00* (2006.01)
*C07H 21/02* (2006.01)
*C07H 21/04* (2006.01)

(52) U.S. Cl.
USPC .......................... 514/44; 536/23.1; 536/24.5

(58) Field of Classification Search
None
See application file for complete search history.

(56) References Cited

U.S. PATENT DOCUMENTS

2008/0214443 A1 *    9/2008    Baum et al. ...................... 514/8

FOREIGN PATENT DOCUMENTS

| EP | 1 535 993 A1 | 6/2005 | |
|----|----|----|----|
| EP | 1 733 718 A1 * | 12/2006 | ...................... 514/44 |
| WO | WO 2004/105737 A2 | 12/2004 | |
| WO | WO 2006/085987 A2 | 8/2006 | |

OTHER PUBLICATIONS

Maksimenko, A. V. et al., "Optimisation of dendrimer-mediated gene transfer by anionic oligomers," *The Journal of Gene Medicine* 2003; 5:61-71.
Mounkes, L. C. et al., "Proteoglycans Mediate Cationic Liposome-DNA Complex-based Gene Delivery in Vitro and in Vivo", *The Journal of Biological Chemistry* 1998; 273(40):26164-26170.

* cited by examiner

*Primary Examiner* — Amy Bowman
(74) *Attorney, Agent, or Firm* — Bruce Vrana

(57) ABSTRACT

The present invention relates to compositions containing a combination of a first active component comprising one or more sulfated polysaccharides and/or glycosaminoglycans and a second active component comprising one or more RNAi-inducing molecules, and methods for using these compositions to enhance double-stranded RNA (dsRNA)-mediated gene silencing in pest or pathogen species. The invention further relates to methods for controlling pests or pathogens, methods for preventing pest infestations or pathogen infections and methods for knocking down gene expression in pests or pathogens using the compositions and methods of the invention.

7 Claims, 13 Drawing Sheets

Fig.1: Dose responses of dextran sulfate (Mw ± 8 kDa) on the RNAi-induced killing of Colorado potato beetle
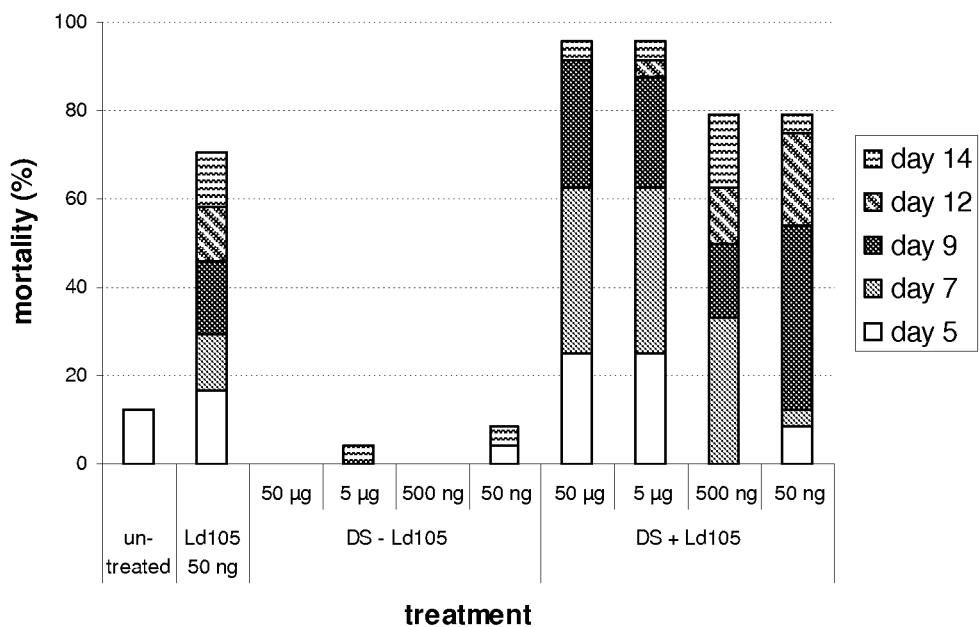
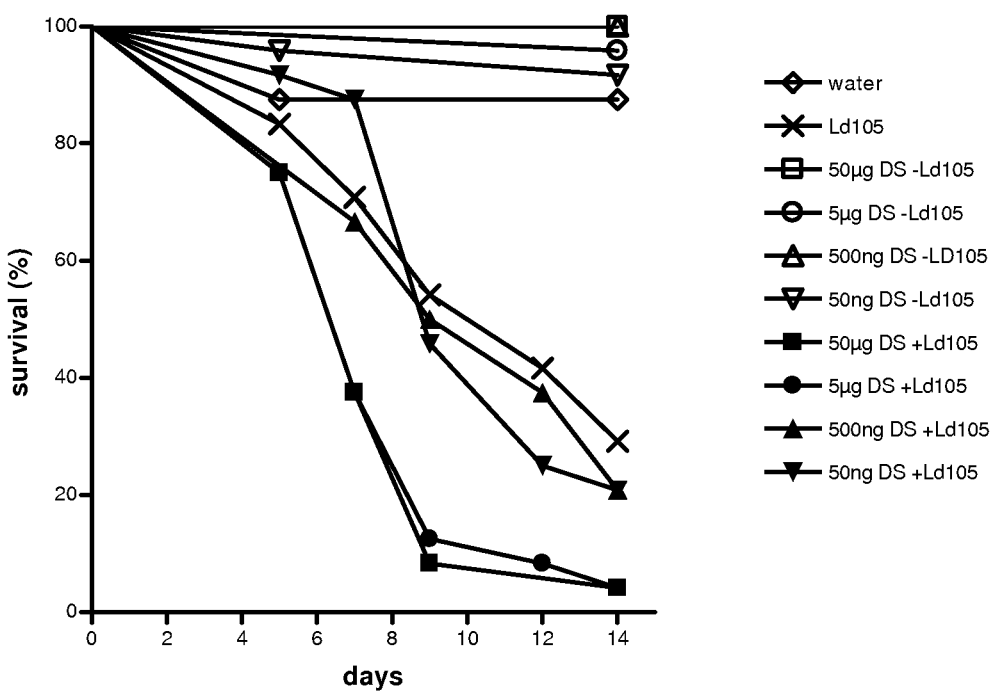

Fig. 2: Dose responses of fucoidan on the RNAi-induced killing of Colorado potato beetle
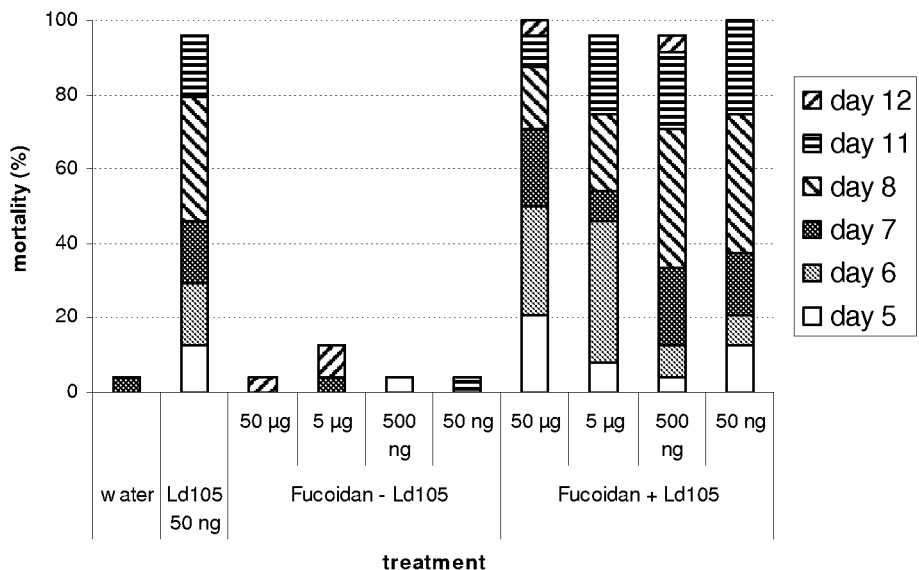
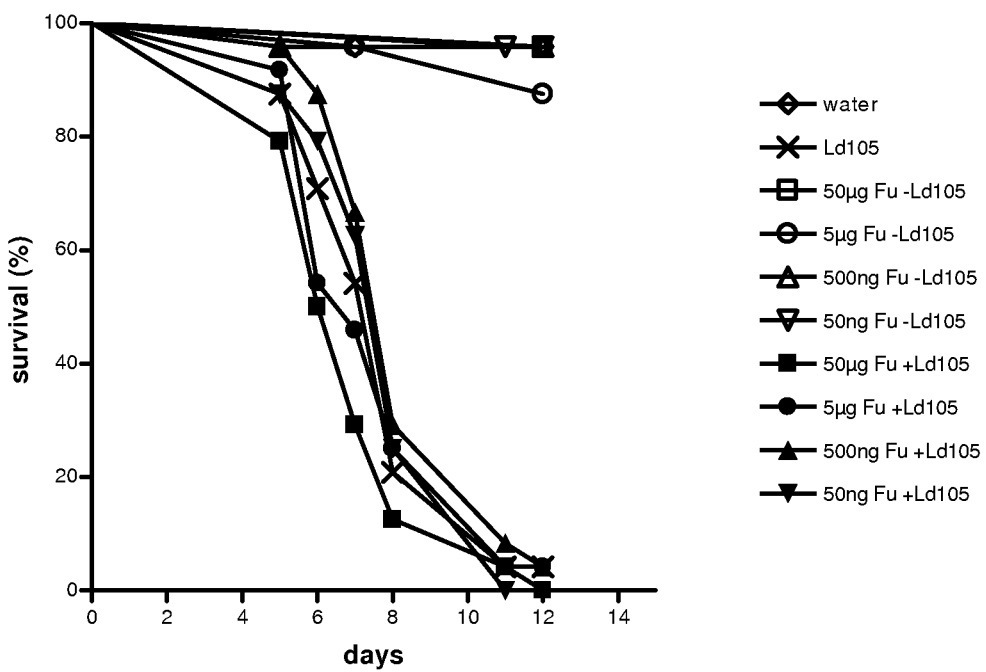

Fig. 3: Dose responses of polyinosine (poly I) on the RNAi-induced killing of Colorado potato beetle
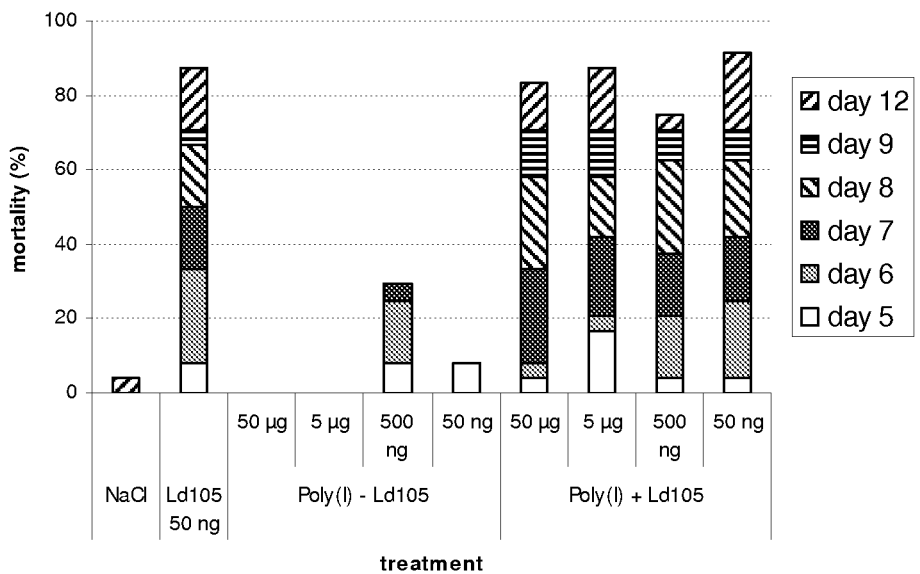
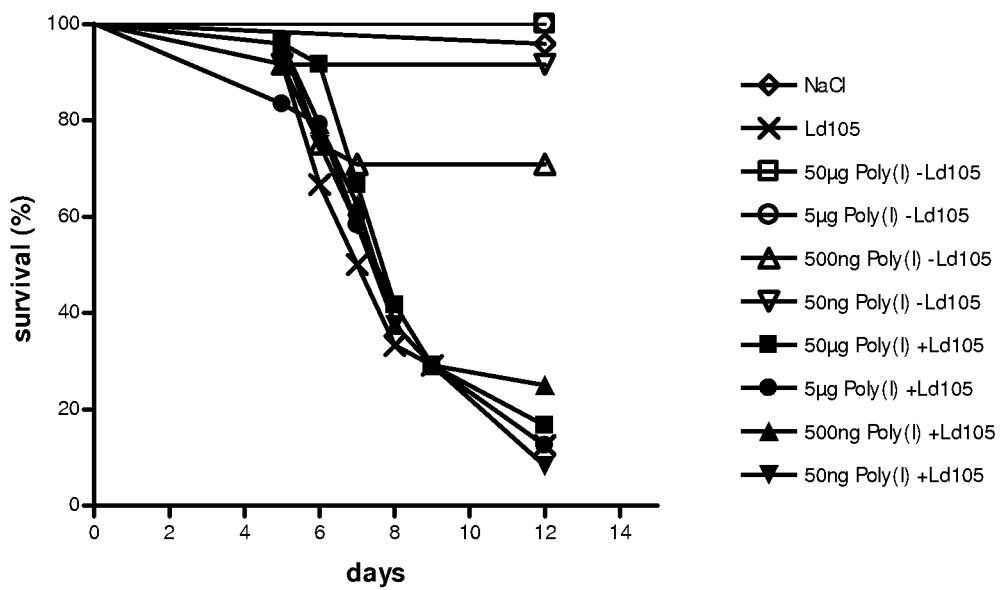

Fig. 4: Dose responses of target dsRNA on the RNAi-induced killing of Colorado potato beetle at one concentration of dextran sulfate
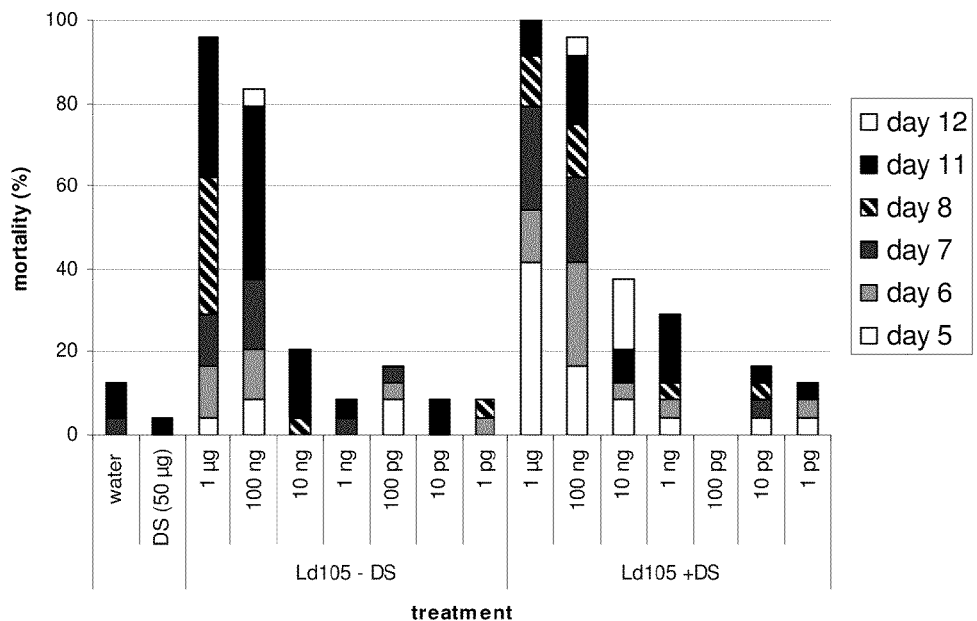
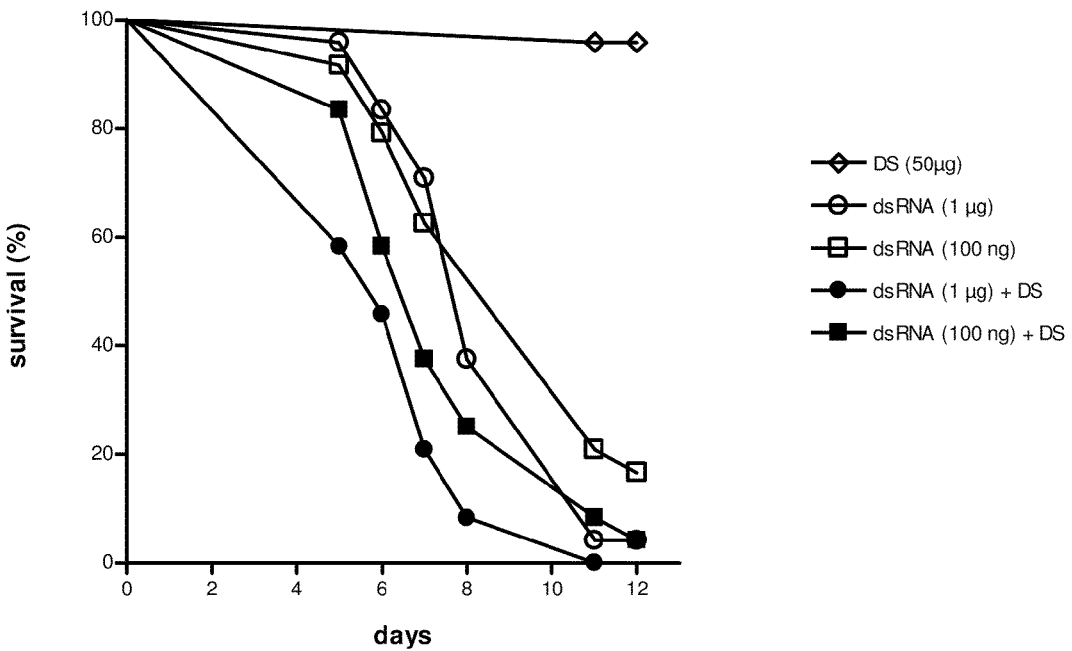

Fig. 5: Dose responses of dextran sulfate (Mw ± 1400 kDa) on the RNAi-induced killing of Colorado potato beetle
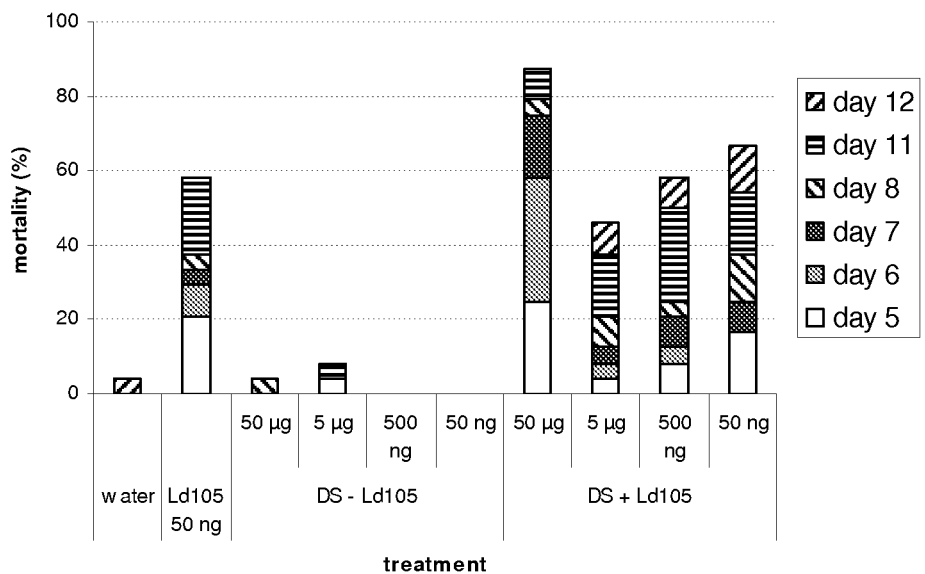

Fig. 6: Dose responses of heparin on the RNAi-induced killing of Colorado potato beetle
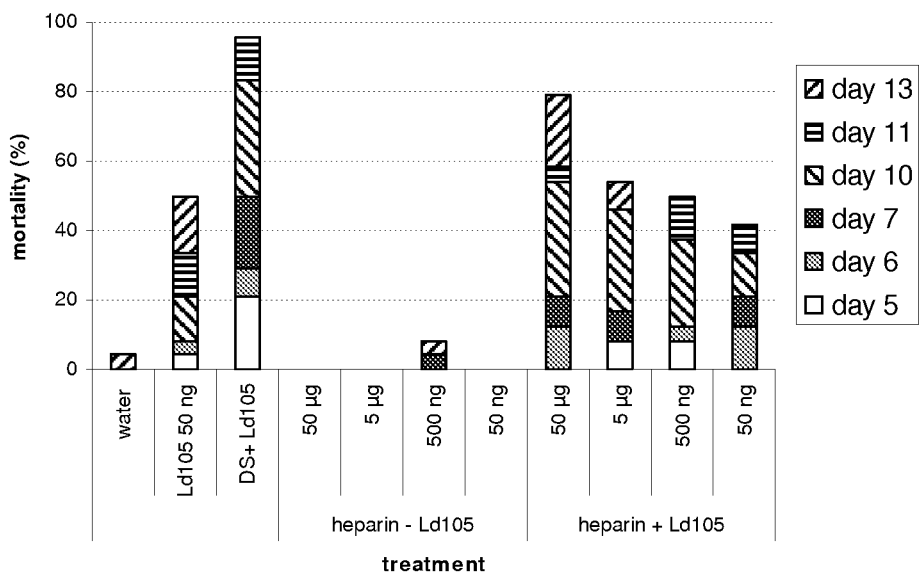
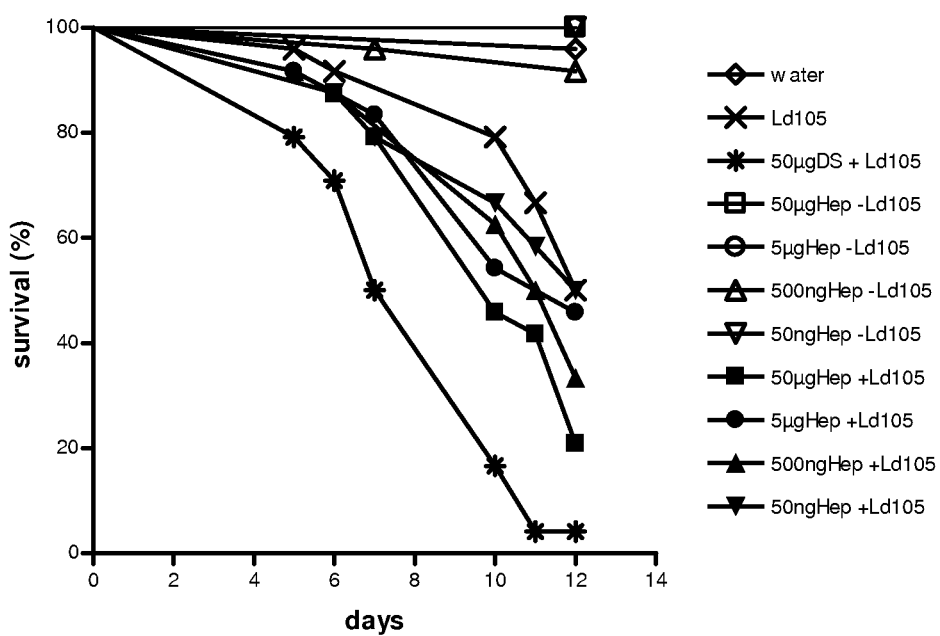

Fig. 7: Dose responses of chondroitin sulfate or hyaluronic acid on the RNAi-induced killing of Colorado potato beetle

Fig. 8: Dose responses of *E. coli* expressed Ld105 double-stranded RNA (SEQ ID NO:1) on the RNAi-induced killing of Colorado potato beetle at one concentration of dextrane sulfate (Mw ± 8 kDa)

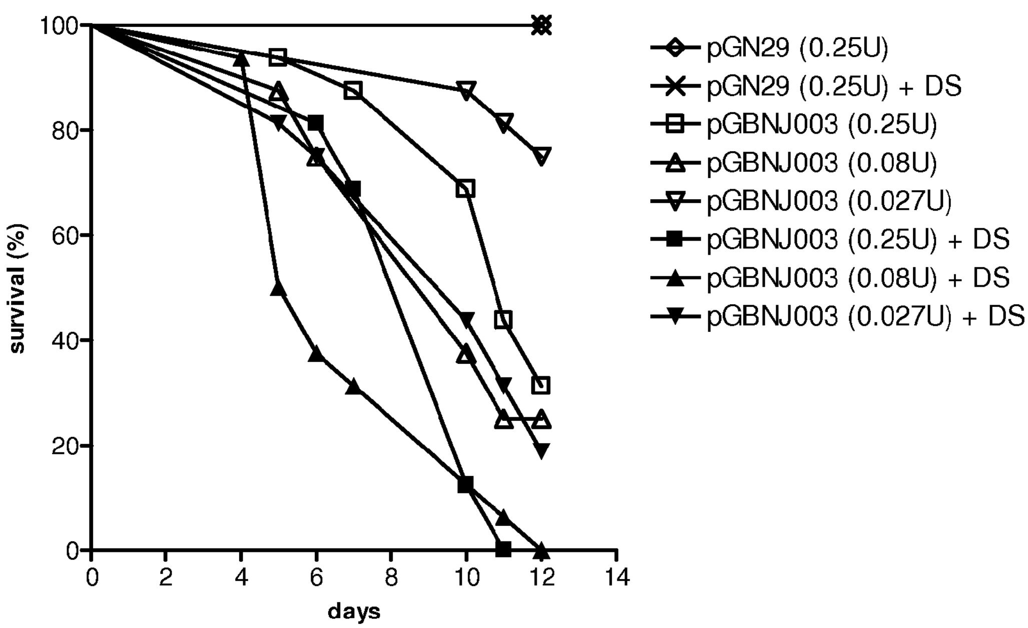

Fig. 9. Effects of dextran sulfate on RNAi-induced killing of Colorado potato beetle by target Ld009, Ld013, Ld105 and Ld248 dsRNAs.
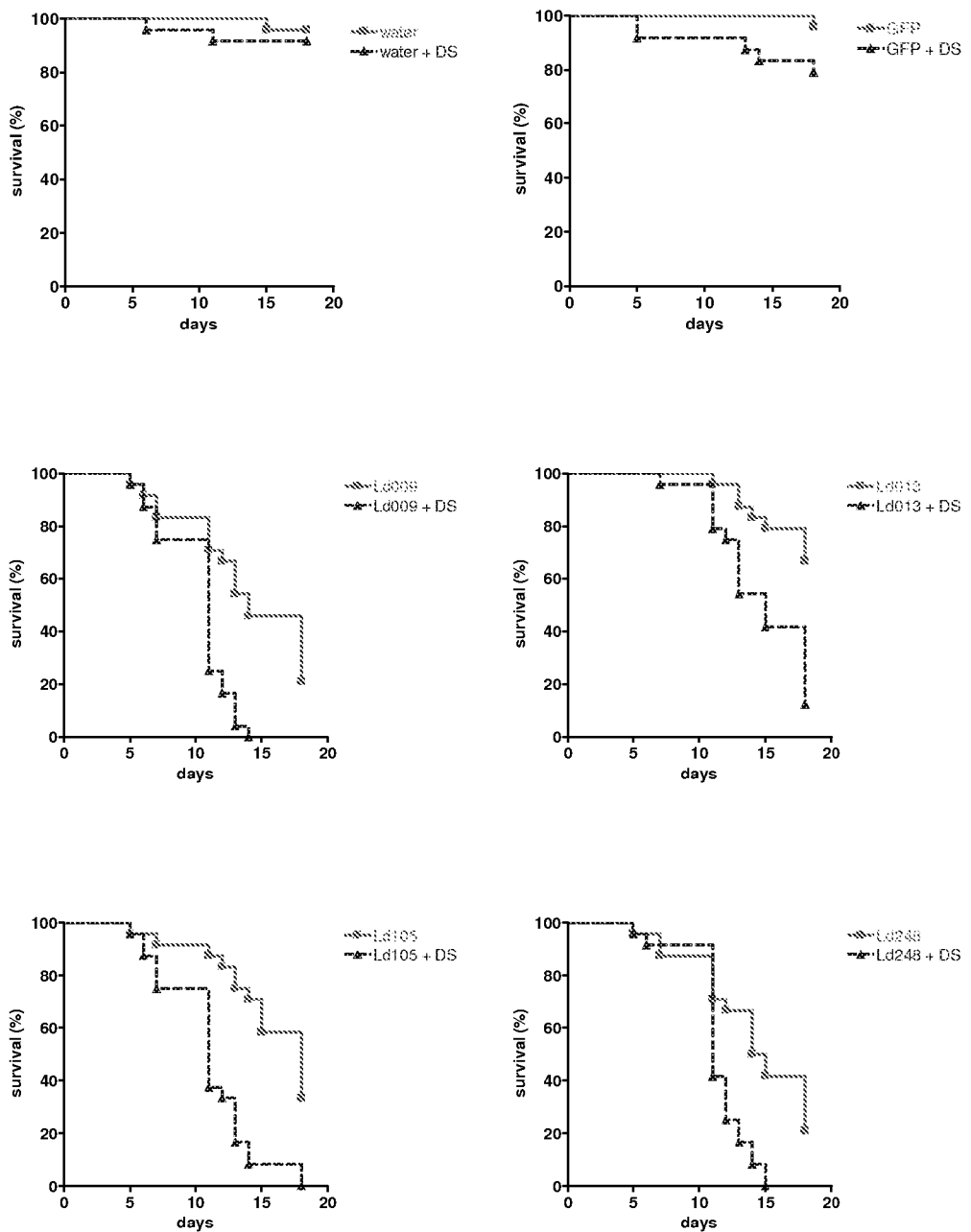

Fig. 10. Effects of dextran sulfate on the RNAi-induced killing of Colorado potato beetle in a leaf-disc bioassay
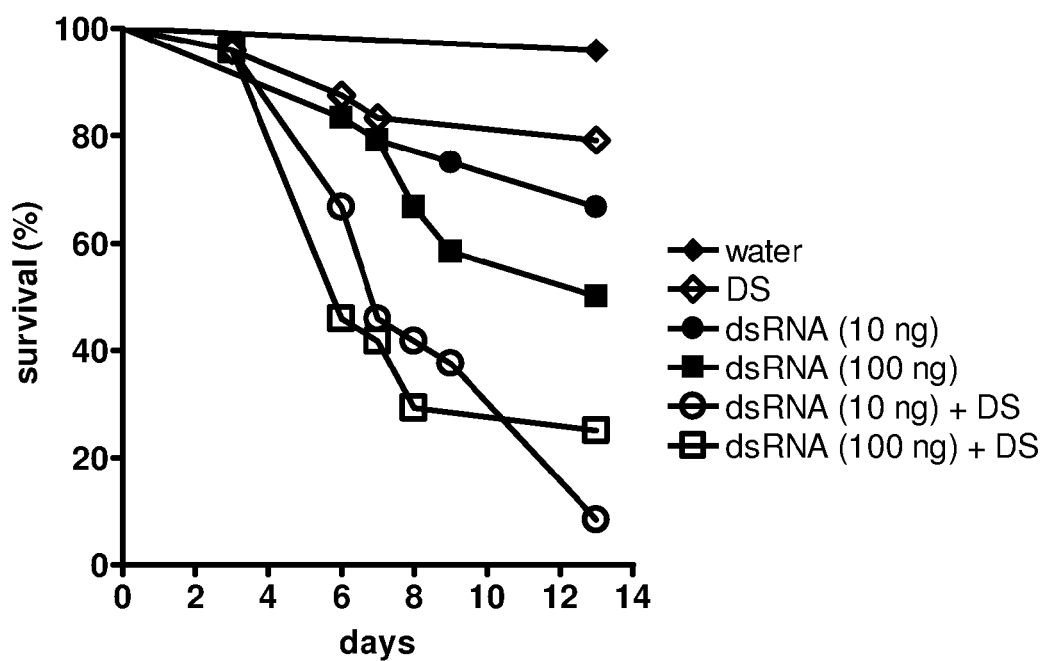

Fig. 11. Effects of priming with dextran sulfate on RNAi-induced killing of Colorado potato beetle
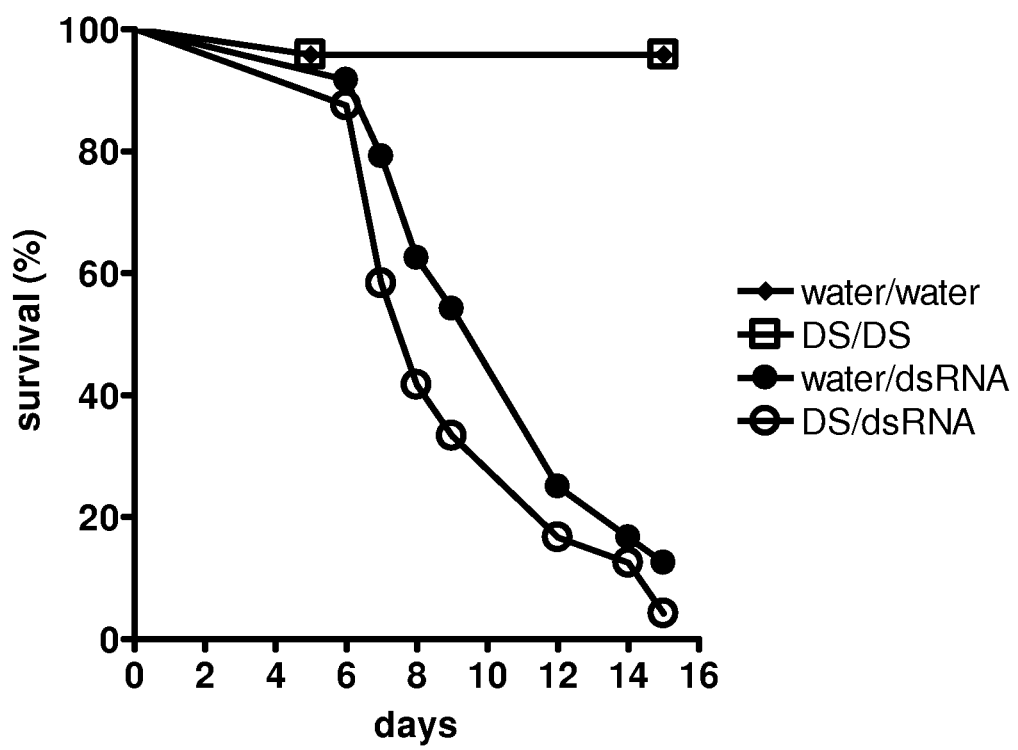

Fig. 12. Effects of dextran sulfate on the RNAi-induced killing of mustard leaf beetle
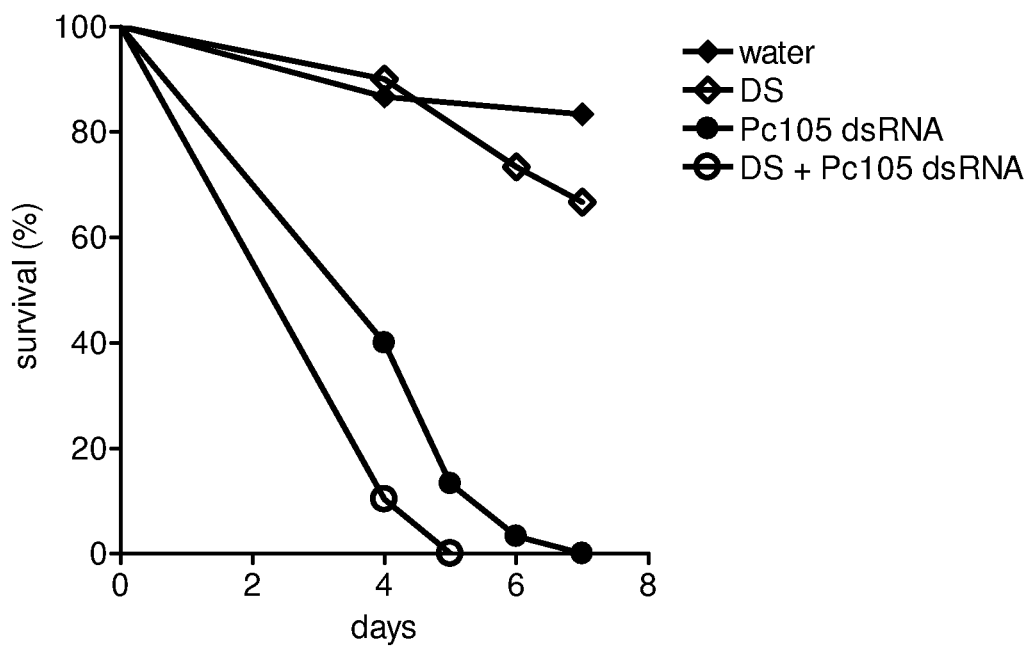

Fig. 13. Effects of dextran sulfate on RNAi-induced phenotype of *Caenorhabditis elegans*.
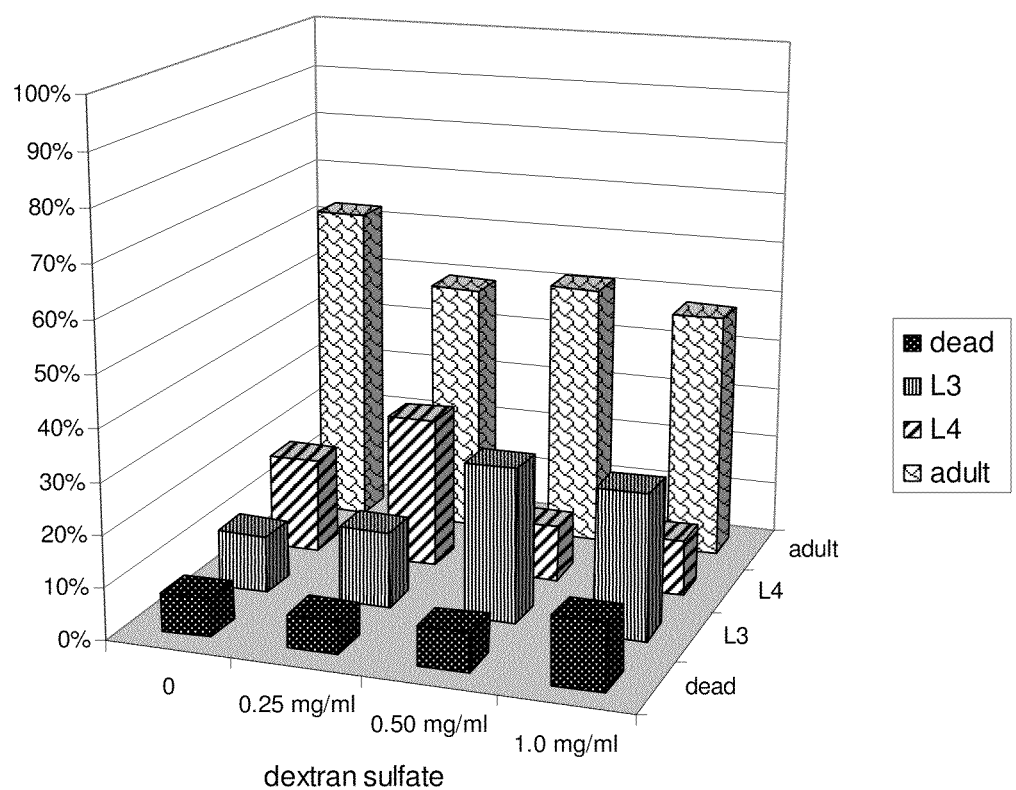

SEQUENCE LISTING

```
<160> NUMBER OF SEQ ID NOS: 6

<210> SEQ ID NO 1
<211> LENGTH: 1504
<212> TYPE: DNA
<213> ORGANISM: Leptinotarsa decemlineata

<400> SEQUENCE: 1
gcttgttgcc cccgaatgcc ttgatagggt tgattacctt tgggaagatg gtccaagtgc      60
acgaactagg taccgagggc tgcagcaaat cttacgtttt ccgagggacg aaagacctca     120
```

```
cagctaagca agttcaagag atgttggaag tgggcagagc cgcagtaagt gctcaacctg    180
ctcctcaaca accaggacaa cccatgaggc ctggagcact ccagcaagct cctacgccac    240
caggaagcag gttccttcaa cccatctcga aatgcgacat gaacctcact gatcttattg    300
gagagttgca aagagaccca tggcctgtcc accaaggcaa atgcgccctt agatcgaccg    360
ggacagcttt atcgatagcc attgggttgt tggagtgcac atacgccaat actggtgcca    420
gggtcatgct attcgttgga ggaccttgct ctcaaggccc tggtcaagtc ttgaatgatg    480
atctgaagca acctatcaga tctcaccacg acatccaaaa agacaatgcc aaatacatga    540
agaaagcaat caagcactat gataaattag cgatgagagc agcaacgaat ggccactgcg    600
ttgacatata ttcatgcgct ttggatcaga caggattgat ggagatgaaa cagtgttgta    660
attcaacagg gggacatatg gtcatgggcg actcgttcaa ttcttccctg ttcaagcaaa    720
cgttccagcg catattttcg aaagatcaga aaaacgagct gaagatggca tttaatggta    780
ctctggaggt caagtgttcc agggagttga aaattcaagg cggtattgga tcttgtgttt    840
cgttgaatgt gaagaatcct ttggtttccg acaccgaaat aggaatgggt aacacggtcc    900
agtggaaaat gtgtacggta actccaagta ctaccatggc cttgttcttc gaggtcgtca    960
accaacattc cgctcccata cctcaagggg aaggggctg catacagttc atcacgcaat   1020
atcagcatgc tagtggccag aagaggatcc gagtaacgac agttgctaga actgggccg    1080 atgcttccgc taatatacat catgtcagtg ctggattcga tcaggaggca gccgcagtga   1140
taatggcgag gatggcagtt tacagagcgg aatcagacga tagccctgat gttttgagat   1200
gggtcgatag gatgttgata cgtctgtgcc agaaattcgg cgaatataac aaggacgacc   1260
cgaattcgtt ccgcttgggc gaaaacttca gcctctaccc gcagttcatg taccatttga   1320
gaaggtcaca gttcctgcag gtgttaaca attctcccga cgaaacgtcc ttctacaggc   1380
acatgcttat gcgcgaagac ctcacgcagt cgctgatcat gatccagccg atactctaca   1440
gctacagttt caatggacca ccagaacctg tgcttttgga tacgagttcc atccaacccg   1500
atag                                                                1504

<210> SEQ ID NO 2
<211> LENGTH: 395
<212> TYPE: DNA
<213> ORGANISM: Leptinotarsa decemlineata

<400> SEQUENCE: 2
ggccccaaga agcatttgaa gcgtttgaat gccccaaaag catggatgtt ggataaattg     60
ggaggtgttt tcgcacctcg cccatctaca ggacctcaca aattgcgaga gtctttgccc    120
ttggtgatct tcctacgtaa ccgattgaag tatgctttga ctaacagcga agttactaag    180
attgttatgc aaaggttaat caaagtagat ggaaaagtga ggaccgactc caattaccct    240
gctgggttta tggatgttat taccattgaa aaaactggtg aatttttccg actcatctat    300
gatgttaaag gacgatttgc agtgcatcgt attactgctg aggaagcaaa gtacaaacta    360
tgcaaagtca ggaggatgca aactggcccc aaagg                               395

<210> SEQ ID NO 3
<211> LENGTH: 203
<212> TYPE: DNA
<213> ORGANISM: Leptinotarsa decemlineata

<400> SEQUENCE: 3
```

```
cgccggagag tttttgtcag cttcttcaaa agctttgcgc aagttactct cagactcgcc    60
agcgagtttg ctcatgatct ccggcccgtt tatcaagaag aagaacgccc cagtctcatt   120
agccacggcg cgagcaatca gggtcttacc cgtaccaggg ggaccataca gcagtatacc   180 cctaggggc ttcacgccga tag                                            203

<210> SEQ ID NO 4
<211> LENGTH: 967
<212> TYPE: DNA
<213> ORGANISM: Leptinotarsa decemlineata

<400> SEQUENCE: 4
gggagcagac gatcggttgg ttaaaatctg ggactatcaa acaaaacgt gtgtccaaac     60 cttggaagga cacgcccaaa acgtaaccgc ggtttgtttc caccctgaac tacctgtggc   120
tctcacaggc agcgaagatg gtaccgttag agtttggcat acgaatacac acagattaga   180
gaattgtttg aattatgggt tcgagagagt gtggaccatt tgttgcttga agggttcgaa   240
taatgtttct ctggggtatg acgagggcag tatattagtg aaagttggaa gagaagaacc   300
ggcagttagt atggatgcca gtggcggtaa aataatttgg gcaaggcact cggaattaca   360
acaagctaat ttgaaggcgc tgccagaagg tggagaaata agagatgggg agcgtttacc   420
tgtctctgta aagatatgg gagcatgtga aatataccct caaacaatcc aacataatcc    480
gaatggaaga ttcgttgtag tatgcggaga cggcgaatat atcatttaca cagcgatggc   540
tctacggaac aaggcttttg gaagcgctca agagtttgtc tgggctcagg actccagcga   600
gtatgccatt cgcgagtctg gttccacaat tcggatattc aaaaacttca agaaaggaa    660 gaacttcaag tcggatttca gcgcggaagg aatctacggg ggttttctct ggggattaa    720 atcggtgtcc ggtttaacgt tttacgattg gaaactttg gacttggtga gacgattga     780 aatacaaccg agggcggttt attggtctga cagtggaaaa ttagtctgtc tcgcaacgga   840
ggacagctac ttcatccttt cttatgattc ggagcaagtt cagaaggcca gggagaacaa   900
tcaagtcgca gaggatggcg tagaggccgc tttcgatgtg ttgggggaaa tgaacgagtc   960
tgtccga                                                             967

<210> SEQ ID NO 5
<211> LENGTH: 1546
<212> TYPE: DNA
<213> ORGANISM: Phaedon cochleariae

<400> SEQUENCE: 5
gctcagccta ttaccgccca acgcgttgat tggattgatc acgttcggaa aaatggtgca    60
agtccacgaa ctgggtaccg aaggctgcag caagtcgtac gtgttctgtg aacgaaaga   120 tctcaccgcc aagcaagtcc aggagatgtt gggcattgga aaagggtcac caaatcccca   180
acaacagcca gggcaacctg gcggccaggg cagaatcccc aagctgccc ctgtaccacc    240 ggggagcaga ttcttgcagc ccgtgtcaaa atgcgacatg aacttgacag atctgatcgg   300
ggagttgcag aaagaccctt ggcccgtaca tcagggcaaa agacctctta gatccacagg   360
cgcagcattg tccatcgctg tcggcctctt agaatgcacc tatccgaata cgggtggcag   420
aatcatgata ttcttaggag gaccatgctc tcagggtccc ggccaggtgt tgaacgacga   480
tttgaagcag cccatcaggt cccatcatga catacacaaa gacaatgcca agtacatgaa   540
gaaggctatc aaacattacg atcacttggc aatgcgagct gccaccaaca gccattgcat   600
cgacatttac tcctgcgccc tggatcagac gggactgatg gagatgaagc agtgctgcaa   660
```

```
ttccaccgga gggcacatgg tcatgggcga ttccttcaat tcctctctat tcaaacaaac    720
cttccagcga gtgttctcaa aagacccgaa gaacgacctc aagatggcgt tcaacgccac    780
cttggaggtg aagtgttcca gggagttaaa agtccaaggg ggcatcggct cgtgcgtgtc    840
cttgaacgtt aaaagccctc tggtttccga tacggaacta ggcatgggga atactgtgca    900
gtggaaactt tgcacgttgg cgccgagctc tactgtggcg ctgttcttcg aggtggttaa    960
ccagcattcg gcgcccatac cacagggagg caggggctgc atccagctca tcacccagta   1020
tcagcacgcg agcgggcaaa ggaggatcag agtgaccacg attgctagaa attgggcgga   1080
cgctactgcc aacatccacc acattagcgc tggcttcgac caagaagcgg cggcagttgt   1140
gatggcccga atggccggtt acaaggcgga atcggacgag actcccgacg tgctcagatg   1200
ggtggacagg atgttgatca ggctgtgcca gaagttcgga gagtacaata aagacgatcc   1260
gaattcgttc aggttggggg agaacttcag tctgtatccg cagttcatgt accatttgag   1320
acggtcgcag tttctgcagg tgttcaataa ttctcctgat gaaacgtcgt tttataggca   1380
catgctgatg cgtgaggatt tgactcagtc tttgatcatg atccagccga ttttgtacag   1440
ttacagcttc aacgggccgc ccgagcctgt gttgttggac acaagctcta ttcagccgga   1500
tagaatcctg ctcatggaca ctttcttcca gatactcatt ttccat                  1546

<210> SEQ ID NO 6
<211> LENGTH: 351
<212> TYPE: DNA
<213> ORGANISM: Caenorhabditis elegans

<400> SEQUENCE: 6
ccgctcgtaa gggaaaggct aaggaggaac aggctgtcgt gtcccttgga ccacaggcca     60
aagaaggaga gctcatcttc ggagtcgctc acatctttgc ttcgttcaac gacactttcg    120
tccacatcac cgatatctca ggacgtgaaa ccatcgttcg agttaccgga ggaatgaagg    180
tcaaggccga tcgtgacgag tcatcgccat acgctgctat gctcgccgct caagacgtcg    240
ctgatcgttg caaacaactc ggaatcaacg ctcttcacat caagcttcgt gctactggag    300
gaaccagaac caagacccca ggaccaggag ctcagtctgc tcttcgtgcc c             351
```

METHODS AND COMPOSITIONS FOR INCREASING RNA INTERFERENCE

RELATED APPLICATIONS

This application claims the benefit under 35 U.S.C. §119(e) of U.S. provisional application 61/030,029, filed Feb. 20, 2008, U.S. provisional application 61/087,315, filed Aug. 8, 2008, and U.S. provisional application 61/118,105, filed Nov. 26, 2008, the entire disclosures of which are incorporated herein by reference.

FIELD OF THE INVENTION

The present invention relates to various compositions containing a combination of (1) one or more sulfated polysaccharides and/or glycosaminoglycans and (2) one or more RNAi-inducing molecules, and methods for using these compositions to enhance double-stranded RNA (dsRNA)-mediated gene silencing in pest and/or pathogen species.

BACKGROUND OF THE INVENTION

Over the last few years, reduction of gene expression (also referred to as "knockdown" or "gene silencing") in multicellular organisms by means of RNA interference or "RNAi" has become a well-established technique. RNAi is a process of sequence-specific knockdown of gene expression initiated by double-stranded RNA (dsRNA) that is complementary in sequence to a region of the target gene to be knocked down (Fire, A. Trends Genet. Vol. 15, 358-363, 1999; Sharp, P. A. Genes Dev. Vol. 15, 485-490, 2001). Reference may also be made to International applications WO 99/32619 (Carnegie Institution) and WO 00/01846 (Devgen NV), and U.S. Pat. No. 6,506,559.

Gene silencing by dsRNA finds application in many different areas, such as dsRNA-mediated gene silencing in clinical applications (WO 2004/001013). The technique of RNAi has also been used to knock down gene expression in pests, including insects. Other published applications that relate to the use of RNAi to protect plants against insects include the International applications WO 2006/046148A2 (Devgen NV); WO 2006/045591A2 (Devgen NV); WO 2006/045590A2 (Devgen NV); WO 2006129204 (Devgen NV); WO 2001/37654 (DNA Plant Technologies), WO 2005/019408 (Bar Ilan University), WO 2005/049841 (CSIRO, Bayer Cropscience), WO 2005/047300 (University of Utah Research foundation), WO 2005/110068 (Monsanto), WO2007/035650 (Monsanto), WO2007/083193 (Devgen NV), WO2007/074405 (Devgen NV), WO2007/080127 (Devgen NV), WO2007/080126 (Devgen NV) and the US published application 2003/00150017 (Mesa et al).

SUMMARY OF THE INVENTION

To date, no methods of pest and/or pathogen control have been described which utilize compounds or compositions that further increase the RNA interference (RNAi) effect of dsRNA, further reduce expression of a selected gene or genes, and thereby further increase the mortality of pests and/or pathogens. In addition, no such methods have been described which utilize compounds or compositions that further increase the RNA interference (RNAi) effect of dsRNA that is expressed by microorganisms such as bacteria. Such methods and compositions would be of benefit by either reducing the amount of dsRNA that is necessary to control pests and/or pathogens, or by increasing the lethality of any given quantity of dsRNA, or by shortening the period to kill the pest and/or pathogen after application of the dsRNA.

In the research leading to identification of RNAi receptors, the present inventors found that certain molecules enhanced the RNAi effect whilst they were searching for molecules that would prevent RNAi. Scavenger receptors have been shown to be implicated in target dsRNA uptake and initiation of RNA interference. Certain polyanions and sulfated polysaccharides are antagonists of scavenger receptors and have been reported to prevent RNA interference when administered in the presence of target dsRNA (Saleh et al., 2006). In addition, the complex branched sulfated polysaccharide dextran sulfate specifically inhibited poly I:C dsRNA activation of intracellular signaling required for cytokine and chemokine secretion via scavenger receptor type SR-A (Limmon et al., 2007). Based on these reports the inventors tested whether scavenger receptor antagonists could prevent target dsRNA from setting off the RNAi process in insecta and thereby demonstrate that these receptors play a pivotal role in initiation of RNA interference. Quite surprisingly, ingestion of target dsRNA in the presence of the sulfated polysaccharide dextran sulfate led to substantially increased lethality when compared to target dsRNA alone. Contrary to the expectations, sulfated polysaccharides, such as dextran sulfate, substantially increased the RNAi-induced lethality of target dsRNA (i.e., insect mortality) when the two components were coadministered in insect feeding bioassays. Additionally, ingestion of target dsRNA in the presence of glycosaminoglycans, such as heparin, also unexpectedly increased insect mortality when compared to target dsRNA alone.

While pest- and/or pathogen-specific target double-stranded RNA molecules (dsRNA), once ingested, have been shown to be lethal by RNA interference (RNAi) to certain pests, the present inventors have now developed methods by which the RNAi-induced lethality of dsRNA and lethality in pests and/or pathogens can be substantially increased by feeding target dsRNA to the pests and/or pathogens in the presence of enhancing molecules or compounds. These methods comprise the feeding to pests and/or pathogens of such enhancing molecules or compounds either before, during, or after the feeding to pests and/or pathogens of either target dsRNA or microorganisms, such as bacteria, which express dsRNA.

This increase in the RNAi-induced mortality in pests and/or pathogens was a surprisingly effective result of feeding both enhancing molecules or compounds and dsRNA or microorganisms which express dsRNA to pest and/or pathogens. Although sulfated compounds have been used to mobilize polynucleotides into cells (e.g. for transfection of cells with nucleic acids), the compositions of the present invention (1) increased the effectiveness of RNAi in pests and/or pathogens, (2) and/or increased the lethality of dsRNA toward pests and/or pathogens, (3) and/or increased the yields of crops that were susceptible to pests and/or pathogens. Furthermore, the above-mentioned results were achieved, unexpectedly, despite the simplicity of the methods of the invention, in which the compositions comprising the enhancing compounds and either target dsRNA or microorganisms expressing such dsRNA are merely sprayed on or near the crops of interest. Moreover, the dsRNA in the composition is not complexed with the enhancing molecules.

The present invention provides a method for substantially increasing the efficiency of controlling pest infestation and/or pathogen infection by RNA interference via contacting an organism or cell, or administering to an organism (e.g. by ingestion), target dsRNA in the presence of enhancing molecules or compounds. The target dsRNA can be in the form of nucleic acid molecules or prokaryotic or eukaryotic cells, such as bacteria or other microorganisms, that express the target dsRNA.

One aspect of the invention includes methods for increasing the RNA interference (RNAi) effect of a molecule or composition that reduces expression of a selected gene or genes by RNA interference in cell(s) or an organism. The methods include contacting the cell(s) or organism with (1) a first active component including an amount of one or more sulfated polysaccharides and/or glycosaminoglycans that is effective to enhance the RNAi effect of the molecules or composition and (2) a second active component including molecules or a composition that reduces expression of a selected gene or genes by RNA interference. In some embodiments of the foregoing methods the cell(s) or organism is contacted with the first active component before or after contacting the cell(s) or organism with the second active component. In further embodiments of the foregoing methods the cell or organism is contacted with the first active component simultaneously with contacting the cell(s) or organism with the second active component. In yet other embodiments of the foregoing methods the cell or organism is contacted with the first active component before, simultaneously with and/or after contacting the cell(s) or organism with the second active component. "Contacting" includes applying or spraying the second active component and the effective amount of the first active component onto the cell(s) or organism or on food for the organism. In embodiments of the foregoing methods the first active component and the second active component are independently applied or the first active component and the second active component are combined in a composition as described herein.

In another aspect of the invention, methods for protecting plants or foodstuffs or substances from pest infestation or pathogen infection are provided. The methods include contacting the plant or soil wherein the plant is rooted, or foodstuff or substance with (1) a first active component including an amount of one or more sulfated polysaccharides and/or glycosaminoglycans that is effective to enhance the RNAi effect of the molecules or composition and (2) a second active component comprising molecules or a composition that reduces expression of a selected gene or genes by RNA interference. In embodiments of the foregoing methods, the plant or soil wherein the plant is rooted, or foodstuff or substance is contacted with the first active component before or after contacting the plant or soil wherein the plant is rooted, or foodstuff or substance with the second active component. In further embodiments of the foregoing methods, the plant or soil wherein the plant is rooted, or foodstuff or substance is contacted with the first active component simultaneously with contacting the plant or soil wherein the plant is rooted, or foodstuff or substance with the second active component. In yet other embodiments of the foregoing methods, the plant or soil wherein the plant is rooted, or foodstuff or substance is contacted with the first active component before, simultaneously with and/or after contacting the plant or soil wherein the plant is rooted, or foodstuff or substance with the second active component. "Contacting" includes applying or spraying the second active component and the effective amount of the first active component onto the plant or foodstuff or substance. In embodiments of the foregoing methods the first active component and the second active component are independently applied or the first active component and the second active component are combined in a composition as described herein.

According to another aspect of the invention, methods for treating a plant infection by a pathogen or plant infestation by a pest are provided. The methods include contacting the plant or the soil wherein the plant is rooted with (1) a first active component including an amount of one or more sulfated polysaccharides and/or glycosaminoglycans that is effective to enhance the RNAi effect of the molecules or composition and (2) a second active component including molecules or a composition that reduces expression of a selected gene or genes by RNA interference. In embodiments of the foregoing methods, the plant or the soil wherein the plant is rooted is contacted with the first active component before or after contacting the plant with the second active component. In other embodiments of the foregoing methods, the plant or the soil wherein the plant is rooted is contacted with the first active component simultaneously with contacting the plant or soil wherein the plant is rooted, with the second active component. In further embodiments of the foregoing methods, the plant or the soil wherein the plant is rooted is contacted with the first active component before, simultaneously with and/or after contacting the plant or soil wherein the plant is rooted, with the second active component. "Contacting" includes applying or spraying the second active component and the effective amount of the first active component onto the plant. In embodiments of the foregoing methods, the first active component and the second active component are independently applied or the first active component and the second active component are combined in a composition as described herein.

According to a further aspect of the invention, methods are provided for increasing crop yield or reducing a decline in crop yield that results from pest infestation and/or pathogen infection, comprising contacting a plant or soil surrounding a plant with a composition. Such compositions include a first active component comprising an amount of one or more sulfated polysaccharides and/or glycosaminoglycans, wherein the amount of one or more sulfated polysaccharides and/or glycosaminoglycans is effective to increase the RNAi effect of a molecule(s) or a composition on a selected gene or genes and a second active component comprising one or more prokaryotic cells or eukaryotic cells or host organisms that express double-stranded RNA molecule(s) that reduce (the) expression of a selected gene or genes by RNA interference (RNAi) in a target cell or target organism. Both the increases in crop yields and the reductions in the decline of crop yields are established from comparisons of yields of crops which have been treated with the compositions described herein relative to the yields of crops which have not been treated with the compositions and methods described herein. Both the increases in crop yields and the reductions in the decline of crop yields are also established from comparisons of yields of crops rooted in soils which have been treated with the compositions and methods described herein relative to the yields of crops rooted in soils which have not been treated with the compositions and methods described herein. Increases in crop yields can range between 1% and 100%, including 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, 120%, 140%, 160%, 180%, 200%, 220%, 240%, 260%, 280%, 300%, 320%, 340%, 360%, 380%, 400%, 420%, 440%, 460%, 480%, 500%, 520%, 540%, 560%, 580%, 600%, 620%, 640%, 660%, 680%, 700%, 720%, 740%, 760%, 780%, 800%, 820%, 840%, 860%, 880%, 900%, 920%, 940%, 960%, 980%, and 1000%. Reductions in the decline of crop yields can range between 1% and 100%, including 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, and 100%.

Another aspect of the invention provides methods for protecting a human or an animal from pest infestation or pathogen infection or methods for treating a pest infestation or pathogen infection of a human or an animal. The methods include administering to the human or animal an effective amount of (1) a first active component comprising an amount of one or more sulfated polysaccharides and/or glycosaminoglycans that is effective to enhance the RNAi effect of the molecules or composition and (2) a second active component including molecules or a composition that reduces expression of a selected gene or genes by RNA interference. In embodiments of the foregoing methods, the human or animal is administered the first active component before or after administering the second active component to the human or animal. In other embodiments of the foregoing methods, the human or animal is administered the first active component simultaneously with administering the second active component to the human or animal. In further embodiments of the foregoing methods, the human or animal is administered the first active component before, simultaneously with and/or after administering the second active component to the human or animal. In other embodiments of the foregoing methods, the administering includes topical, parenteral, enteral, transdermal, cutaneous, subcutaneous, intravenous, intraperitoneal, intramuscular or oral administration. In embodiments of the foregoing methods the first active component and the second active component are independently applied or the first active component and the second active component are combined in a composition as described herein.

In another aspect of the invention, methods for the preparation of a medicament for preventing or treating a pest infestation or pathogen infection of a human or an animal are provided, these medicaments comprising an effective amount of (1) a first active component comprising an amount of one or more sulfated polysaccharides and/or glycosaminoglycans that is effective to enhance the RNAi effect of the molecules or composition and (2) a second active component comprising molecules or a composition that reduces expression of a selected gene or genes by RNA interference.

According to another embodiment, medicaments are provided comprising an effective amount of (1) a first active component comprising an amount of one or more sulfated polysaccharides and/or glycosaminoglycans that is effective to enhance the RNAi effect of the molecules or composition, and (2) a second active component comprising molecules or a composition that reduces expression of a selected gene or genes by RNA interference. In embodiments of the foregoing is the medicament formulated for topical, parenteral, enteral, transdermal, cutaneous, subcutaneous, intravenous, intraperitoneal, intramuscular or oral administration.

According to another aspect of the invention, compositions are provided. The compositions include a first active component including an amount of one or more sulfated polysaccharides and/or glycosaminoglycans, wherein the amount of one or more sulfated polysaccharides and/or glycosaminoglycans is effective to increase the RNAi effect of a molecule(s) or a composition on a selected gene or genes; and a second active component comprising (i) at least one RNA molecule of which at least a portion is a double stranded RNA (dsRNA) molecule; or (ii) one or more prokaryotic cells or eukaryotic cells or host organisms that express double-stranded RNA molecule(s) that reduce expression of a selected gene or genes by RNA interference (RNAi) in a pest and/or pathogen cell or organism.

In some embodiments, the first active component is one or more sulfated polysaccharides or one or more glycosaminoglycans or a combination thereof. In preferred embodiments, the first active component is dextran sulfate, or fucoidan, or heparin. More preferably, the dextran sulfate has an average molecular weight of about between 8 and 40 kilodaltons.

In other embodiments of the foregoing compositions, the second active component expresses at least one RNA molecule of which at least a portion is double-stranded (dsRNA) or is a double-stranded RNA molecule. Preferably, the dsRNA molecules are dsRNA molecules consisting of two separate strands, siRNA molecules or hairpin molecules.

In still other embodiments of the foregoing compositions, the one or more prokaryotic or eukaryotic cells of the second active component comprise an expression vector that expresses at least one RNA molecule of which at least a portion is double-stranded. Preferably the expression vector includes at least one regulatory sequence operably linked to the nucleotide sequence encoding the at least one RNA molecule and which nucleotide sequence is complementary to at least part of the nucleotide sequence of a selected gene or genes to be knocked down.

In yet other embodiments of the foregoing compositions, the second active component includes one or more prokaryotic cells or eukaryotic cells or host organisms that express the double-stranded RNA. Preferably the prokaryotic cell is a bacterial cell. Preferably the bacterial cell is an *Escherichia coli* (*E. coli*) cell. Preferably the eukaryotic cell is a yeast cell.

In yet other embodiments of the foregoing compositions, at least one strand of the dsRNA includes a nucleotide sequence that is complementary to a portion of the nucleotide sequence of a selected gene or genes from the pest and/or pathogen cell or organism.

In some embodiments of the foregoing compositions, the gene or genes is/are essential for the viability, growth, development or reproduction of the pest and/or pathogen cell or organism. Preferably, the gene or genes in the second active component comprise at least one nucleic acid comprising (i) the sequence of any of SEQ ID NOs 1 to 6, (ii) the rNA equivalent thereof, (iii) the complement of (i) or (ii), or (iv) a fragment of any of (i) to (iii) consisting of at least 17 contiguous nucleotides of any of (i) to (iii).

In some embodiments of the foregoing compositions, the pest and/or pathogen cells or organisms are pest species, pathogen species, or cells thereof. Preferably, the pest or pathogen is a fungus, an insect or a nematode.

In some embodiments of the foregoing compositions, the first active component is present in an amount of 0.000001%-99% by weight of the composition (W/W), or preferably 0.00001%-99% by weight (W/W), or more preferably, 0.0001%-99% by weight (W/W), or still more preferably 0.0002%-99% by weight (W/W). In some embodiments of the foregoing compositions, the second active component is present in an amount of 0.0000000001%-99% by weight (W/W) of the composition, or preferably 0.000000001%-99% by weight (W/W), or more preferably 0.00000001%-99% by weight (W/W).

In additional embodiments, the foregoing compositions consist essentially of the first and second active components as described above.

According to another aspect of the invention, kits are provided. The kits include a first container containing an amount of a first active component including one or more sulfated polysaccharides and/or glycosaminoglycans as provided in any of the foregoing compositions, and a second container including a second active component comprising a molecule(s) or a composition that reduces expression of a selected gene or genes by RNA interference (RNAi) in a pest and/or pathogen cell or organism as provided in any of the foregoing compositions. The amount of one or more sulfated polysaccharides and/or glycosaminoglycans is effective to increase the RNAi effect of the molecule(s) or composition.

According to another aspect of the invention, methods for making a RNAi composition are provided. The methods include combining a first active component including an amount of the one or more sulfated polysaccharides and/or glycosaminoglycans as provided in any of the foregoing compositions, and a second active component including a molecule(s) or a composition that reduces expression of a selected gene or genes by RNA interference (RNAi) in a pest and/or pathogen cell or organism as provided in any of the foregoing compositions, to make a RNAi composition. The amount of one or more sulfated polysaccharides and/or glycosaminoglycans is effective to increase the RNAi effect of the molecule(s) or composition on the selected gene or genes.

These and other aspects of the invention will be described in greater detail below.

BRIEF DESCRIPTION OF THE DRAWINGS

FIG. 1 shows survival of *L. decemlineata* larvae on artificial diet treated with target Ld105 double-stranded RNA (SEQ ID NO:1) in the presence of varying amounts of dextran sulfate (Mw±8 kDa). On the artificial diet, each larva was exposed to water only, 50 ng target Ld105 dsRNA only (designated as Ld105), 50 µg, 5 µg, 500 ng or 50 ng dextran sulfate in the absence (designated as DS–Ld105) or presence (designated as DS+Ld105) of 50 ng target Ld105 dsRNA. Twenty-four larvae were tested per condition. Number of survivors were assessed on 5, 7, 9, 12 and 14 days post infestation. Mortality versus treatment and survival curves are shown.

FIG. 2 shows survival of *L. decemlineata* larvae on artificial diet treated with target Ld105 double-stranded RNA (SEQ ID NO:1) in the presence of varying amounts of fucoidan. On the artificial diet, each larva was exposed to water only, 50 ng target Ld105 dsRNA only (designated as Ld105), 50 µg, 5 µg, 500 ng or 50 ng fucoidan in the absence (designated as Fucoidan–Ld105) or presence (designated as Fucoidan+Ld105) of 50 ng target Ld105 dsRNA. Twenty-four larvae were tested per condition. Number of survivors were assessed on 5, 6, 7, 8, 11 and 12 days post infestation. Mortality versus treatment and survival curves are shown.

FIG. 3 shows survival of *L. decemlineata* larvae on artificial diet treated with target Ld105 double-stranded RNA (SEQ ID NO:1) in the presence of varying amounts of the polyanion, polyinosine. On the artificial diet, each larva was exposed to 0.9 M NaCl only (designated as NaCl), 50 ng target Ld105 dsRNA only (designated as Ld105), 50 µg, 5 µg, 500 ng or 50 ng polyinosine in the absence (designated as Poly(I)–Ld105) or presence (designated as Poly(I)+Ld105) of 50 ng target Ld105 dsRNA. Twenty-four larvae were tested per condition. Number of survivors were assessed on 5, 6, 7, 8, 9 and 12 days post infestation. Mortality versus treatment and survival curves are shown.

FIG. 4 shows survival of *L. decemlineata* larvae on artificial diet treated with target Ld105 double-stranded RNA (SEQ ID NO:1) at different amounts in the presence of dextran sulfate (Mw±8 kDa) at one quantity. On the artificial diet, each larva was exposed to water only, 50 µg of dextran sulfate only (designated as DS), or 1 µg to 1 pg in ten-fold serial dilutions of target Ld105 dsRNA in the absence (designated as Ld105–DS) or presence (designated as Ld105+DS) of 50 µg dextran sulfate. Twenty-four larvae were tested per condition. Number of survivors were assessed on 5, 6, 7, 8, 11 and 12 days post infestation. Mortality versus treatment and survival curves are shown (only selected data represented in the latter figure).

FIG. 5 shows survival of *L. decemlineata* larvae on artificial diet treated with target Ld105 double-stranded RNA (SEQ ID NO:1) in the presence of varying amounts of dextran sulfate (Mw±1400 kDa). On the artificial diet, each larva was exposed to water only, 50 ng target Ld105 dsRNA only (designated as Ld105), 50 µg, 5 µg, 500 ng or 50 ng dextran sulfate in the absence (designated as DS–Ld105) or presence (designated as DS+Ld105) of 50 ng target Ld105 dsRNA. Twenty-four larvae were tested per condition. Number of survivors were assessed on 5, 6, 7, 8, 11 and 12 days post infestation. Mortality versus treatment and survival curves are shown.

FIG. 6 shows survival of *L. decemlineata* larvae on artificial diet treated with target Ld105 double-stranded RNA (SEQ ID NO:1) in the presence of varying amounts of heparin. On the artificial diet, each larva was exposed to water only, 50 ng target Ld105 dsRNA only (designated as Ld105), 50 µg, 5 µg, 500 ng or 50 ng heparin in the absence (designated as heparin–Ld105) or presence (designated as DS+Ld105) of 50 ng target Ld105 dsRNA. Twenty-four larvae were tested per condition. Number of survivors were assessed on 5, 6, 7, 10, 11 and 13 days post infestation. Mortality versus treatment and survival curves are shown.

FIG. 7 shows survival curves of *L. decemlineata* larvae on artificial diet with target Ld105 double-stranded RNA (SEQ ID NO:1) in the presence of chondroitin sulfate or hyaluronic acid. On the artificial diet, each larva was exposed to water only, 50 ng Ld105 dsRNA in the absence or presence of 50 µg chondroitin sulfate (CS) or hyaluronic acid (HA). Twenty-four larvae were tested per condition. Numbers of survivors were assessed regularly for up to 13 days in the bioassay.

FIG. 8 shows survival curves of *L. decemlineata* larvae on artificial diet treated with *E. coli*-expressed Ld105 double-stranded RNA (SEQ ID NO:1) at different amounts in the presence of dextran sulfate (Mw±8 kDa) at one quantity. On the diet, each larva was exposed to 0.25 U pGN29 control, 0.25 U pGBNJ003, 0.08 U pGBNJ003 or 0.027 U pGBNJ003 with or without 50 µg dextran sulfate (DS). One unit (U) corresponds to the amount of bacteria present in 1 mL culture with an OD600 nm value of 1 prior to heat-inactivation. Sixteen larvae were tested per condition. Numbers of survivors were assessed regularly for up to 12 days in the bioassay.

FIG. 9 shows survival of *L. decemlineata* larvae on artificial diet treated with different target double-stranded RNAs (SEQ ID NO:1, 2, 3, 4; Ld105 dsRNA=SEQ ID NO:1, Ld013=SEQ ID NO:2, Ld009=SEQ ID NO:3 and Ld248=SEQ ID NO:4) at one quantity (100 ng) in the presence of dextran sulfate (DS; ±8 kDa) at once quantity (50 µg). On the artificial diet, each larva was exposed to water only or water plus dextran sulfate, gfp dsRNA only or gfp dsRNA plus dextran sulfate, Ld009 dsRNA only or Ld009 dsRNA plus dextran sulfate, Ld013 dsRNA only or Ld013 dsRNA plus dextran sulfate, Ld105 dsRNA only or Ld105 dsRNA plus dextran sulfate, Ld248 dsRNA only or Ld248 dsRNA plus dextran sulfate. Twenty-four larvae were tested per condition. Number of survivors were assessed on 5, 6, 7, 11, 12, 13, 14, 15 and 18 days post infestation. Survival curves for each target dsRNA shown.

FIG. 10 shows survival of L. decemlineata larvae on potato leaf discs treated with target Ld105 double-stranded RNA (SEQ ID NO:1) at different amounts in the presence of dextran sulfate (Mw±8 kDa) at one quantity. Each larva was first exposed to leaf discs treated with water only, 50 µg dextran sulfate only (DS), 10 ng Ld105 dsRNA only, 100 ng Ld105 dsRNA only, 10 ng Ld105 dsRNA plus 50 µg dextran sulfate, or 100 ng Ld105 dsRNA plus 50 µg dextran sulfate. Twenty-four larvae were tested per condition. After 24 hours, each larva was transferred to untreated leaf discs. This was repeated once before transferring them each to a well containing artificial diet. Number of survivors were assessed on 2, 3, 6, 7, 8, 9 and 13 days post infestation (starting on treated leaf discs). Survival curves are shown.

FIG. 11 shows survival of L. decemlineata larvae on artificial diet in a sequential feeding assay with dextran sulfate (DS; ±8 kDa) and target Ld105 double-stranded RNA (SEQ ID NO:1). First, each larva was exposed to artificial diet topically applied with either dextran sulfate or water only. After two full days of feeding, each larva was then transferred to fresh artificial diet topically applied with target Ld105 dsRNA, dextran sulfate or water only. Thus the treatments were with first component/second component: water/water, DS/DS, water/dsRNA, and DS/dsRNA. Amount of dextran sulfate used was 50 µg and target Ld105 dsRNA 1 µg. Twenty-four larvae were tested per condition. Number of survivors were assessed on 5, 6, 7, 8, 9, 12, 14 and 15 days post infestation. Survival curves are shown.

FIG. 12 shows survival of P. cochleariae larvae on oilseed rape leaf discs treated with target Pc105 double-stranded RNA (SEQ ID NO:5) at one quantity (50 ng) in the presence of dextran sulfate (Mw±8 kDa) at one quantity (50 ng). Each larva was first exposed to leaf discs treated with 25 µl of 0.05% Triton X-100 solution with water only (designated water), dextran sulfate only (designated DS), Pc105 dsRNA only or Pc105 dsRNA in combination with dextran sulfate. Thirty larvae were tested per condition. Once the treated leaf disc was consumed by each larva, the larvae were transferred to untreated leaf discs. This was repeated until the end of the bioassay. Number of survivors were assessed on 4, 5, 6 and 7 days post infestation. Survival curves are shown.

FIG. 13 shows survival and developmental stages of C. elegans soaked in target rps-14 double-stranded RNA (SEQ ID NO:6) at one concentration (50 ng/µl) in the presence of different concentrations of dextran sulfate (Mw±8 kDa). Percentage of survival numbers and developmental stages of the nematodes were assessed. AD: adults; L4: fourth larval stage; L3: third larval stage; dead: non-living and/or missing nematodes calculated by subtracting total numbers of L3+L4+AD from the starting count.

DETAILED DESCRIPTION OF THE INVENTION

The invention provides compositions and methods based on the discovery that certain sulfated polysaccharides and glycosaminoglycans increase the RNAi effect of target dsRNA. Therefore, the invention includes compositions containing two "active components" including (1) one or more sulfated polysaccharides and/or glycosaminoglycans and (2) one or more RNAi-inducing double-stranded RNA (dsRNA) molecules. The present invention also includes methods for increasing RNA interference by the application of (1) one or more sulfated polysaccharides and/or glycosaminoglycans and (2) one or more RNAi-inducing double-stranded RNA (dsRNA) molecules. In certain embodiments, the methods for increasing RNA interference-induced effects include increasing dsRNA-mediated gene silencing in particular for the control of pests and/or pathogens, including insects, nematodes, and fungi, in particular for the protection of plants from infestation and/or damage by such pests and/or pathogens.

As indicated, compositions of the invention contain two "active components". The "first active component" is one or more sulfated polysaccharides and/or glycosaminoglycans and the "second active component" is one or more nucleic acid molecules that induces RNA interference, as is well known in the art, and in particular embodiments is one or more RNA molecules of which at least a portion is double-stranded. The sequence of one of the strands of the dsRNA corresponds to part or whole of an essential pest and/or pathogen gene and causes knockdown of this pest and/or pathogen gene expression via RNA interference. As a result of mRNA knockdown the dsRNA reduces or prevents expression of the target pest and/or pathogen protein and, hence, causes death, growth arrest or sterility of the pest and/or pathogen.

The dsRNA-induced RNA interference is rendered more effective when the dsRNA, is coadministered in the presence of one or more various sulfated polysaccharides and/or glycosaminoglycans. In which the presence of sulfated polysaccharides and/or glycosaminoglycans, the effectiveness of dsRNA increases such that a lesser amount can be used to knock down gene expression in a pest and/or pathogen. For example, in the context of protecting plants against insects and other plant pests and/or pathogens, the use of sulfated polysaccharides and/or glycosaminoglycans in combination with dsRNA increases the effectiveness of the dsRNA and/or increases the speed of killing or disabling the plant pests and/or pathogens.

The methods of the invention can find practical applications in any area of technology where it is desirable to inhibit viability, growth, development or reproduction of a pest, or to decrease pathogenicity or infectivity of a pathogen. The methods of the invention further find practical applications where it is desirable to specifically knock down expression of one or more genes in a pest and/or pathogen. Particularly useful practical applications include, but are not limited to, (1) protecting plants against pest infestation or pathogen infection; (2) pharmaceutical or veterinary use in humans and animals (for example, to control, treat or prevent pest or pathogen infections in humans and animals); (3) protecting materials against damage caused by pests or pathogens; (4) protecting perishable materials (such as foodstuffs, seed, etc.) against damage caused by pests or pathogens; (5) generally any application wherein pests or pathogens need to be controlled and/or wherein damage caused by pests or pathogens needs to be reduced or prevented; (6) reducing the amount of dsRNA that is necessary to induce RNAi due to the added effectiveness of compositions comprising both active components, the target dsRNA and one or several sulfated polysaccharides and/or glycosaminoglycans; (7) increasing the speed-to-RNAi-induced-lethality of pest(s) or pathogen(s) utilizing a composition comprising both active components, the target dsRNA and one or more sulfated polysaccharides and/or glycosaminoglycans (8) reducing the time-to-kill of pest(s) or pathogen(s) utilizing a composition comprising both active components, the target dsRNA and one or more sulfated polysaccharides and/or glycosaminoglycans.

Compositions of the invention include two "active components": (1) one or more sulfated polysaccharides and/or glycosaminoglycans, such as but not limited to dextran sulfate, fucoidan or heparin, and (2) one or more molecules or a composition that reduce expression of a selected gene or genes by RNA interference in a cell or organism. The amount of one or more sulfated polysaccharides and/or glycosaminoglycans is present in an amount that is effective to increase the RNAi effect of the molecule(s) or composition on the selected gene or genes.

The "first active component" of the invention comprises one or more sulfated polysaccharides and/or glycosaminoglycans. "Sulfated polysaccharides" as used in the application are relatively complex carbohydrates containing up to 30% sulfur by weight. Polysaccharides are polymers made up of many monosaccharides joined together by glycosidic bonds. They are often branched, and therefore large macromolecules. Polysaccharides have a general formula of $C_n(H_2O)_{n-1}$ where n is usually a large number between 200 and 2500. Considering that the repeating units in the polymer backbone are often six-carbon monosaccharides, the general formula can also be represented as $(C_6H_{10}O_5)_n$ where n={40 . . . 3000}.

One example of sulfated polysaccharides are "dextran sulfates", which are long-chain polymers of glucose containing approximately 10-40% of sulfur. Preferably the dextran sulfates contain approximately 17-20% of sulfur, many of which are commercially available. Low molecular weight dextran sulfates have a molecular weight ranging from about 5000 to about 10000 daltons whereas high molecular weight dextran sulfates can go to 2000 kilodaltons (kDa). As illustrated later on, any of the molecular weight variants of dextran sulfate can be used in the methods and compositions of the invention. Another example of a sulfated polysaccharide is fucoidan, which consists in two distinct forms: F-fucoidan, which is >95% composed of sulfated esters of fucose, and U-fucoidan, which is approximately 20% glucuronic acid.

"Glycosaminoglycans" (also known as GAGs or mucopolysaccharides) belong to the family of polysaccharides and are long unbranched polysaccharides consisting of a repeating disaccharide unit. This unit consists of N-acetyl-hexosamine and a hexose or hexuronic acid, either or both of which may be sulfated. As used herein, the term "sulfated glycosaminoglycans" means glycosaminoglycans that are sulfated. The family of sulfated glucosaminoglycans, therefore, overlaps with the family of sulfated polysaccharides. Heparin is a highly-sulfated glycosaminoglycan consisting of a variably-sulfated repeating disaccharide unit having a molecular weight ranging from about 3 kDa to about 40 kDa. Hyaluronan is the only GAG that is exclusively not sulfated. Average molecular weights of the sulfated glycosaminoglycans can be any known in the art. Preferably the average molecular weight of glycosaminoglycans is between about 500 daltons and about 3000 kilodaltons.

Some of these compounds, such as dextrane sulfate and fucoidan are known as complexing agents for complexing nucleic acids upon transfection of cells. Surprisingly, these compounds are now demonstrated to enhance the RNA interference effect when they are fed in combination to pest organisms such as insects and nematodes. Moreover, the ingestion of dsRNA in the presence of sulfated polysaccharides and/or glycosaminoglycans reaches the appropriate target sites to initiate the systemic RNAi effect resulting in increased and/or more efficient lethality of the pest organism.

Sulfated polysaccharides and/or glycosaminoglycans may be obtained from natural sources, such as from naturally occurring organisms, recombinant organisms, synthetic methods, or any combination thereof.

In preferred embodiments, the "second active component" of the invention comprises RNA molecules of which at least a portion is double-stranded. Examples of double-stranded RNA molecules are small interfering RNA (siRNA) molecules, hairpin RNA (hpRNA) molecules, etc. Other examples are well known in the art. The expression "at least part" or "at least a portion" as used herein means for instance over at least 15, 16, 17, 18, 19, 20, 21, 22, 23, 24 or more contiguous nucleotides, preferably at least 30, 50, 100, or at least 150 contiguous nucleotides.

The RNA molecule that reduces expression of a selected gene or genes by RNA interference effect in a target cell or target organism may also be, or be produced by, an expression vector that expresses a double-stranded RNA. Such RNA molecules may be provided as cells that harbor the expression vector. Thus, the molecules or composition can be one or more prokaryotic host cells (such as bacterial cells), eukaryotic host cells (such as yeast cells) or host organisms that express the double-stranded RNA. In such embodiments, the double-stranded RNA typically is expressed from a recombinant construct, which construct includes at least one regulatory sequence operably linked to the nucleotide sequence which is complementary to at least part of the nucleotide sequence of a selected gene or genes to be knocked down. Such expression vectors, cells and organisms are well known in the art, for example, as described in WO 2001/088121 and WO 2000/001846, both of Devgen NV.

In addition, any suitable double-stranded RNA fragment capable of directing RNAi or RNA-mediated gene silencing or inhibition of a pest and/or pathogen gene may be used in the methods of the invention.

In more detailed terms, the invention provides for host cells and/or RNA molecules comprising a nucleotide sequence that is the RNA complement of or that represents the RNA equivalent of at least part of the nucleotide sequence of a target gene from a target pest and/or pathogen organism, as produced by transcription of a nucleic acid molecule.

The term "complementary" relates to any of DNA-DNA complementarity, DNA-RNA complementarity, and RNA-RNA complementarity. In analogy herewith, the term "RNA complement" or "RNA equivalent" substantially means that in the DNA sequence(s), the base "T" may be replaced by the corresponding base "U" normally present in ribonucleic acids.

In preferred embodiments as shown in the Examples below, the RNA molecules used as the second active component or expressed by any of the cell(s) therein, is any of SEQ ID NOs 1 to 6. For instance, SEQ ID NO 1 is the partial sense strand of a gene that is a GTPase activator of Leptinotarsa decemlineata (see also WO2007/083193 from DEVGEN, NV). For application in the present invention are included: all dsRNA molecules comprising (or being complementary to) at least part of any of SEQ ID NOs 1 to 6, as well as all partial sequences/fragments that show at least 80% identity, more preferably at least 85% identity, still more preferably at least 90% identity, still more preferably at least 95% identity, still more preferably at least 98% identity, and most preferably at least 99% identity to any of SEQ ID NOs 1 to 6 (over the length of the fragment). Percent identity can be calculated using methods well known in the art, for example, as described in Dufresne et al 2002 Nature Biotechnol. 20: 1269-1271. Also included for use as the second active component are orthologous sequences of other insects, nematodes or fungi (see also WO2007/083193 from DEVGEN, NV). In addition, any of the sequences with SEQ ID NOs 1 to 2481, any complements or fragments thereof as described in the WO2007/083193 publication from applicant can be used in the methods and compositions described in the present application and included herein by reference.

The "second active component" of the compositions and methods of the invention may comprise isolated double-stranded RNA comprising annealed complementary strands, one of which has a nucleotide sequence which is complementary to at least part of a target nucleotide sequence of a gene of a pest or pathogen. The gene may be any of the (target) genes known in the art, or a part thereof that exerts the same function. Preferred target sequences are exemplified in WO2007/083193.

The double-stranded RNA comprises annealed complementary strands, one of which has a nucleotide sequence which corresponds to a target nucleotide sequence of the gene to be knocked down. The other strand of the double-stranded RNA is able to base-pair, at least in part, with the first strand.

The present invention relates to any gene of interest (which may be referred to herein as the "target gene") that can be knocked down.

The (target) gene(s) against which the "second active component," or the dsRNA, is directed is/are selected as being essential for the viability, growth, development or reproduction of the cell or organism. The cell or organism that is targeted by the RNA molecules of the invention preferably is a pest or pathogen species. Pests or pathogens may be, for example, selected from fungi, insects and nematodes.

The terms "knockdown of gene expression", "inhibition of gene expression" and the like are used interchangeably and refer to a measurable or observable reduction in gene expression or a complete abolition of detectable gene expression, at the level of protein product and/or mRNA product from the (target) gene. Knockdown or inhibition of gene expression is "specific" when knockdown or inhibition of the (target) gene occurs without manifested effects on other genes of the targeted cell or organism.

The term "knockdown of gene expression" implies reduced expression of one or more genes of an organism due to the action of a dsRNA such as a short DNA or RNA oligonucleotide with a sequence complementary to a gene or its mRNA transcripts. During a gene knockdown event, the binding of this dsRNA to the gene or its transcripts causes decreased expression through blocking of transcription.

Depending on the nature of the (target) gene, knockdown or inhibition of gene expression in cells of an organism such as a pest or pathogen can be confirmed by phenotypic analysis of a cell or the whole pest or pathogen or by measurement of mRNA or protein expression using molecular techniques such as RNA solution hybridization, nuclease protection, Northern hybridization, reverse transcription polymerase chain reaction, gene expression monitoring with a microarray, antibody binding, enzyme-linked immunosorbent assay (ELISA), Western blotting, radioimmunoassay (RIA), other immunoassays, or fluorescence-activated cell analysis (FACS).

For targeting pests or pathogens, the "gene" or "target gene" may be essentially any gene that it is desirable to be inhibited because it interferes with growth or pathogenicity or infectivity of the pest or pathogen. For instance, if the method of the invention is to be used to prevent insect growth and/or infestation then it is preferred to select a (target) gene which is essential for viability, growth, development or reproduction of the insect, or any gene that is involved with the insect's ability to infest, such that specific inhibition of the (target) gene leads to a lethal phenotype or decreases or stops insect infestation.

According to one non-limiting embodiment, the (target) gene is such that when its expression is knocked down or inhibited using the method of the invention, the pest or pathogen is killed, or the reproduction or growth of the pest or pathogen is stopped or retarded. This type of (target) gene is considered to be essential for the viability of the pest or pathogen and is referred to as essential genes. Therefore, the present invention encompasses a method as described herein, wherein the (target) gene is an essential gene.

According to a further non-limiting embodiment, the (target) gene is such that when it is knocked down using the method of the invention, the infestation or infection by the pest or pathogen, the damage caused by the pest or pathogen, and/or the ability of the pest or pathogen to infest or infect host organisms and/or cause such damage, is reduced. The terms "infest" and "infect" or "infestation" and "infection" are generally used interchangeably throughout. This type of (target) gene is considered to be involved in the pest's ability to infest or in the pathogenicity or infectivity of the pathogen. Therefore, the present invention extends to methods as described herein, wherein the (target) gene is involved in the pest's ability to infest or in the pathogenicity or infectivity of the pathogen. The advantage of choosing the latter type of (target) gene is that the pest or pathogen is blocked to infest or infect further organisms and to form further generations.

According to one embodiment, (target) genes are conserved genes, pest-specific genes or pathogen-specific genes.

The expression "target region" or "target nucleotide sequence" of the pest/pathogen (target) gene may be any suitable region or nucleotide sequence of the gene. The target region should comprise at least 17, at least 18 or at least 19 consecutive nucleotides of the (target) gene, more preferably at least 20 or at least 21 nucleotide and still more preferably at least 22, 23 or 24 nucleotides of the (target) gene.

It is preferred that at least part of the double-stranded RNA will share 100% sequence identity with the target region of the pest or pathogen (target) gene. However, it will be appreciated that 100% sequence identity over the whole length of the double stranded RNA is not essential for functional RNA inhibition. RNA sequences with insertions, deletions, and single point mutations relative to the target sequence have also been found to be effective for RNA inhibition. The terms "corresponding to" or "complementary to" are used interchangeably herein, and when these terms are used to refer to sequence correspondence between the double-stranded RNA and the target region of the (target) gene, they are to be interpreted accordingly, i.e. as not absolutely requiring 100% sequence identity. However, the percent sequence identity between the double-stranded RNA and the target region will generally be at least 50% to 85% identical, preferably at least 90%, 95%, 96%, or more preferably at least 97%, 98% and still more preferably at least 99%. One preferred way of calculating sequence identity is as described in Dufresne et al 2002 Nature Biotechnol. 20: 1269-1271. Preferred sequences that are useful in accordance with the invention to produce a dsRNA for use in the compositions and methods described herein are any of SEQ ID NO 1 to 6, or any of SEQ ID NOs 1 to 2481, any complements or fragments thereof as described in the WO2007/083193.

Although the dsRNA contains a sequence which corresponds to the target region of the (target) gene it is not absolutely essential for the whole of the dsRNA to correspond to the sequence of the target region. For example, the dsRNA may contain short non-target regions flanking the target-specific sequence, provided that such sequences do not affect performance of the dsRNA in RNA inhibition to a material extent.

The dsRNA may contain one or more substitute bases in order to optimize performance in RNAi. It will be apparent to the skilled reader how to vary each of the bases of the dsRNA in turn and test the activity of the resulting siRNAs (e.g. in a suitable in vitro test system) in order to optimize the performance of a given dsRNA.

The dsRNA may further contain DNA bases, non-natural bases or non-natural backbone linkages or modifications of the sugar-phosphate backbone, for example, to enhance stability during storage or enhance resistance to degradation by nucleases.

It has also recently been suggested that synthetic RNA duplexes consisting of either 27-mer blunt or short hairpin (sh) RNAs with 29 bp stems and 2-nt 3' overhangs are more potent inducers of RNA interference than conventional 21-mer siRNAs. Thus, molecules based upon the targets identified above and being either 27-mer blunt or short hairpin (sh) RNAs with 29-bp stems and 2-nt 3' overhangs are also included within the scope of the invention.

Therefore, in one embodiment, the double-stranded RNA fragment (or region) will itself preferably be at least 17 base pairs (bp) in length, preferably 18 or 19 bp in length, more preferably at least 20 bp, more preferably at least 21 bp, or at least 22 bp, or at least 23 bp, or at least 24 bp, 25 bp, 26 bp or at least 27 bp in length. The expressions "double-stranded RNA fragment" or "double-stranded RNA region" refer to a small entity of the double-stranded RNA corresponding with (part of) the (target) gene.

Generally, the double stranded RNA is preferably between about 17-15000 bp, even more preferably between about 80-12000 bp and most preferably between about 17-27 bp or between about 80-1000 bp; such as double stranded RNA regions of about 17 bp, 18 bp, 19 bp, 20 bp, 21 bp, 22 bp, 23 bp, 24 bp, 25 bp, 27 bp, 50 bp, 80 bp, 100 bp, 150 bp, 200 bp, 250 bp, 300 bp, 350 bp, 400 bp, 450 bp, 500 bp, 550 bp, 600 bp, 650 bp, 700 bp, 900 bp, 100 bp, 1100 bp, 1200 bp, 1300 bp, 1400 bp, 1500 bp, 2000 bp, 2500 bp, 3000 bp, 4500 bp, 5000 bp, 5500 bp, 6500 bp, 7000 bp, 8000 bp, 9000 bp, 10000 bp, 11000 bp, 12000 bp, 13000 bp, 14000 bp or 15000 bp. Exemplary sequences that can be used to produce double-stranded RNA are SEQ ID NOs 1 to 6, or any of SEQ ID NOs 1 to 2481, any complements or fragments thereof as described in the WO2007/083193.

The double-stranded RNA may be fully or partially double-stranded. Partially double-stranded RNAs may include short single-stranded overhangs at one or both ends of the double-stranded portion, provided that the RNA is still capable of being taken up by the pest or pathogen and directing RNAi. The double-stranded RNA may also contain internal non-complementary regions.

The "second active component" of compositions and methods of the invention encompasses the simultaneous or sequential provision of two or more different double-stranded RNAs or RNA constructs to the same pest or pathogen, so as to achieve knockdown or inhibition of multiple (target) genes or to achieve a more potent inhibition of a single (target) gene.

Alternatively, multiple targets are hit by the provision of one double-stranded RNA that hits multiple target sequences. Alternatively, a single target is more efficiently inhibited by the presence of more than one copy of the double-stranded RNA fragment corresponding to the (target) gene. Thus, in one embodiment of the invention, the double-stranded RNA construct comprises multiple dsRNA regions, at least one strand of each dsRNA region comprising a nucleotide sequence that is complementary to at least part of a target nucleotide sequence of a pest or pathogen (target) gene. According to the invention, the dsRNA regions in the RNA construct may be complementary to the same or to different (target) genes and/or the dsRNA regions may be complementary to (target) genes from the same or from different pest or pathogen species. The use of such dsRNA constructs in an application on a cell or organism (such as a plant) or a substrate susceptible to pest or pathogen infestation and/or infection, can establish a more potent resistance to a single pest or pathogen or to multiple pest or pathogen species.

In one embodiment, the double-stranded RNA region comprises multiple copies of the nucleotide sequence that is complementary to the (target) gene. The "second active component" of compositions of the invention thus encompasses isolated double-stranded RNA constructs comprising at least two copies of said nucleotide sequence complementary to at least part of a nucleotide sequence of a pest or pathogen target.

The term "multiple" in the context of the present invention means at least two, at least three, at least four, at least five, at least six, etc.

DsRNA that hits more than one of the above-mentioned targets, or a combination of different dsRNA against different of the above mentioned targets are developed and used in the methods of the present invention. Alternatively, the dsRNA hits more than one target sequence of the same (target) gene.

Accordingly, the "second active component" of the present invention extends to isolated dsRNAs or RNA constructs wherein the dsRNA comprises annealed complementary strands, one of which has a nucleotide sequence which is complementary to at least part of a target nucleotide sequence of a pest or pathogen (target) gene, and which comprises the RNA equivalents of at least two nucleotide sequences independently chosen from each other, or preferably at least three, four or five, independently chosen nucleotide sequences or fragments thereof of at least 17 (contiguous) basepairs in length, preferably at least 18, 19, 20 or 21, more preferably at least 22, 23 or 24 basepairs in length thereof, or more preferably at least 50, 100 or 150 bp thereof.

At least two nucleotide sequences may be derived from any of the (target) genes herein described. According to one preferred embodiment, the dsRNA hits at least one (target) gene that is essential for viability, growth, development or reproduction of the pest or pathogen and hits at least one gene involved in the pest's ability to infest or pathogenicity or infectivity of the pathogen as described hereinabove. Alternatively, the dsRNA hits multiple genes of the same category, for example, the dsRNA hits at least two essential genes or at least two genes involved in. According to a further embodiment, the dsRNA hits at least two (target) genes, which (target) genes are involved in a different cellular function. The dsRNA regions (or fragments) in the double-stranded RNA may be combined as described in detail in WO2006/046148 the contents of which are incorporated herein by reference, which RNA constructs can be used in the methods and compositions of the invention.

Preferably, all double-stranded RNA regions of the "second active component" of the invention comprise at least one strand that is complementary to at least part or a portion of the nucleotide sequence of any of the (target) genes herein described. However, provided one of the double-stranded RNA regions comprises at least one strand that is complementary to a portion of the nucleotide sequence of any one of the (target) genes herein described, the other double-stranded RNA regions may comprise at least one strand that is complementary to a portion of any other pest or pathogen (target) gene (including known (target) genes).

Also provided in the "second active component" of described compositions and methods are isolated double-stranded RNA constructs, further comprising at least one additional sequence and optionally a linker. In one embodiment, the additional sequence is chosen from the group comprising (i) a sequence facilitating large-scale production of the dsRNA construct; (ii) a sequence effecting an increase or decrease in the stability of the dsRNA; (iii) a sequence allowing the binding of proteins or other molecules to facilitate uptake of the RNA construct by pests or pathogens; (iv) a sequence which is an aptamer that binds to a receptor or to a molecule on the surface or in the cytoplasm of a pest or pathogen to facilitate uptake, endocytosis and/or transcytosis by the pest or pathogen; or (v) additional sequences to catalyze processing of dsRNA regions. In one embodiment, the linker is a conditionally self-cleaving RNA sequence, preferably a pH-sensitive linker or a hydrophobic sensitive linker. In another embodiment, the linker is an intron.

In one embodiment of the "second active component," multiple dsRNA regions of the double-stranded RNA construct are connected by one or more linkers. In another embodiment, the linker is present at a site in the RNA construct, separating the dsRNA regions from another region of interest. Different linker types for use in the dsRNA molecules of the invention are described in detail in WO2006/046148 the contents of which are incorporated herein by reference.

In one particular embodiment of the "second active component" of the invention, dsRNA constructs are provided with an aptamer to facilitate uptake of the dsRNA by the cell or organism, such as a pest or pathogen. The aptamer is designed to bind a substance which is taken up by the pest or pathogen. Such substances may be from a pest or pathogen or plant origin. One specific example of an aptamer, is an aptamer that binds to a transmembrane protein, for example a transmembrane protein of a pest or pathogen. Alternatively, the aptamer may bind a (plant) metabolite or nutrient which is taken up by the pest or pathogen. Aptamers for use in the present invention are in detail described in WO2006/045590 the contents of which are incorporated herein by reference.

Without wishing to be bound by any particular theory or mechanism, it is thought that "second active component," the double-stranded RNAs, are taken up by a pest or pathogen from their immediate environment in the presence of the "first active component" of the invention. Double-stranded RNAs taken up into the gut and transferred to the gut epithelial cells are then processed within the cell into short double-stranded RNAs, called small interfering RNAs (siRNAs), by the action of an endogenous endonuclease. The resulting siRNAs then mediate RNAi via formation of a multi-component RNase complex termed the RISC or RNA interfering silencing complex.

The dsRNA may be formed from two separate (sense and antisense) RNA strands that are annealed together by (non-covalent) basepairing. Alternatively, the dsRNA may have a foldback stem-loop or hairpin structure, wherein the two annealed strands of the dsRNA are covalently linked. In this embodiment the sense and antisense stands of the dsRNA are formed from different regions of single polynucleotide molecule that is partially self-complementary. RNAs having this structure are convenient if the dsRNA is to be synthesized by expression in vivo, for example in a host cell or organism, or by in vitro transcription. The precise nature and sequence of the "loop" linking the two RNA strands is generally not material to the invention, except that it should not impair the ability of the double-stranded part of the molecule to mediate RNAi. The features of "hairpin" or "stem-loop" RNAs for use in RNAi are generally known in the art (see for example WO 99/53050, the contents of which are incorporated herein by reference). In other embodiments of the invention, the loop structure may comprise linker sequences or additional sequences as described above.

The double-stranded RNA or construct may be prepared in a manner known per se. For example, double-stranded RNAs may be synthesized in vitro using chemical or enzymatic RNA synthesis techniques well known in the art. In one approach the two separate RNA strands may be synthesized separately and then annealed to form double-strands. In another embodiment, double-stranded RNAs or constructs may be synthesized by intracellular expression in a host cell or organism from one or more suitable expression vectors. This approach is discussed in further detail below.

The amount of the "second active component," e.g. the double-stranded RNA, with which the pest or pathogen is in contact is such that specific knockdown of the one or more (target) genes is achieved. The RNA may be introduced in an amount which allows delivery of at least one copy. However, in certain embodiments higher doses (e.g., at least 5, 10, 100, 500 or 1000 copies) of dsRNA may yield more effective inhibition. For any given pest or pathogen gene target the optimum amount of dsRNA for effective inhibition may be determined by routine experimentation.

The pest or pathogen can be contacted with the sulfated polysaccharides and/or glycosaminoglycans together with the dsRNA in any suitable manner, permitting direct uptake of the dsRNA by the pest or pathogen. For example, the pest or pathogen can be contacted with the dsRNA in pure or substantially pure form, for example, an aqueous solution containing the dsRNA. In this embodiment, the pest or pathogen may be simply "soaked" with an aqueous solution comprising the dsRNA. In a further embodiment the pest or pathogen can be contacted with the dsRNA by spraying the pest or pathogen with a liquid composition comprising the double-stranded RNA.

Alternatively, the sulfated polysaccharides and/or glycosaminoglycans and/or the double-stranded RNA may be linked to a food component of the pests or pathogens, such as a food component for a mammalian pathogenic pest, in order to increase uptake of the dsRNA by the pest or pathogen.

The compositions of the invention can include various amounts and ratios of the "two active components." For example, the "first active component," one or more sulfated polysaccharides and/or glycosaminoglycans, can be present in an amount of between about 0.000001%-99% by weight of the composition (W/W), preferably 0.00001%-99% by weight (W/W), more preferably, 0.0001%-99% by weight (W/W), still more preferably 0.0002%-99% by weight (W/W). The "second active component," the RNA molecule, can be present in an amount of between about 0.0000000001%-99% by weight (W/W) of the composition, preferably 0.000000001%-99% by weight (W/W), more preferably 0.00000001%-99% by weight (W/W). Higher relative weight percentages may be used when the second active component is considered to be cells or organisms that express dsRNA, such as a bacterium harboring an expression vector that is constructed to produce dsRNA complementary to a (target) gene. Lower relative weight percentages may be used when the second active component is synthetic molecules, such as a synthetic short oligonucleotide (e.g., double-stranded or hairpin RNA) that is complementary to a (target) gene. The referenced amounts can be applied or administered in one or more applications or doses given over time.

The invention also provides methods for making compositions of at least two active components, including (1) an amount of one or more sulfated polysaccharides and/or glycosaminoglycans as described herein and (2) a molecule(s) or compositions that reduce expression of a selected gene or genes by RNA interference. The amount of the one or more sulfated polysaccharides and/or glycosaminoglycans is sufficient to be effective to increase the RNAi effect of the molecule(s) or composition on the selected gene or genes.

Methods for increasing an RNA interference effect of a molecule or composition that reduces expression of a selected gene or genes in cell(s) or an organism also are provided. The methods generally include contacting cell(s) or organism with molecules or a composition that reduces expression of a selected gene or genes by RNA interference and an amount of one or more sulfated polysaccharides and/or glycosaminoglycans that is effective to enhance the RNAi effect of the molecules or composition. The properties of the RNAi molecules or compositions and the sulfated polysaccharides and/or glycosaminoglycans are described elsewhere herein.

The methods may be practiced by contacting the cells or organisms with the two active components in combination or in any order, as long as at least some of the sulfated polysaccharides and/or glycosaminoglycans are present at the same time as at least some of the RNAi molecules. Thus, the cell(s) or organism can be contacted with the one or more sulfated polysaccharides and/or glycosaminoglycans before or after contacting the cell(s) or organism with the RNAi molecules. The cell or organism also can be contacted with the one or more sulfated polysaccharides and/or glycosaminoglycans simultaneously with the RNAi molecules. Combinations of the contacting schemes can be used also. For example, the cell or organism can be contacted with the one or more sulfated polysaccharides and/or glycosaminoglycans before, simultaneously with and after contacting the cell(s) or organism with the RNAi molecules.

Contacting the cell(s) or organism with the RNAi molecules and the sulfated polysaccharides and/or glycosaminoglycans can be carried out by any convenient method(s) known to the skilled person. For example, the molecules or composition and the one or more sulfated polysaccharides and/or glycosaminoglycans can be applied by soaking or spraying onto the cell(s) or organism. When the organism is a human or animal, i.e., for therapeutic use, the first and second active components can be administered to the human or animal by standard routes of administration as are well known in the art. Additional methods will be known to the skilled person.

In other embodiments, the pest or pathogen may be contacted with a composition containing the two active components of the invention. The composition may, in addition to the two active components, contain further excipients, diluents or carriers. Preferred features of such compositions are discussed in more detail below.

The sulfated polysaccharides and/or glycosaminoglycans and/or the double-stranded RNA may also be incorporated in the medium in which the pest or pathogen grows or in or on a material or substrate that is infested or infected by the pest or pathogen, respectively, or impregnated in a substrate or material susceptible to infestation or infection by pest or pathogen.

The composition may be provided in a form wherein it actively expresses the "second active component," the double-stranded RNA, e.g. the composition may be a cell harboring an expression vector expressing dsRNA. The cell may be a eukaryotic or prokaryotic cell. Alternatively, the cell may be "capable of expressing", meaning that it is transformed with a transgene which encodes the desired dsRNA but that the transgene is not active in the cell when (and in the form in which) the cell is supplied. In preferred embodiments, when the "second active component" comprises eukaryotic or prokaryotic cells harboring or expressing the dsRNA is killed or heat-inactivated prior to application on the plant, the animal or human or the substrate to be treated or to be applied to.

Therefore, according to another embodiment, a recombinant DNA construct is provided comprising the nucleotide sequence encoding the dsRNA or dsRNA construct according to the present invention operably linked to at least one regulatory sequence. Preferably, the regulatory sequence is selected from the group comprising constitutive promoters or inducible promoters as are well known in the art and as are described herein.

The (target) gene may be any (target) gene known to persons skilled in the art. The term "regulatory sequence" is to be taken in a broad context and refers to a regulatory nucleic acid capable of effecting expression of the sequences to which it is operably linked.

Encompassed by the aforementioned term are promoters and nucleic acids or synthetic fusion molecules or derivatives thereof which activate or enhance expression of a nucleic acid, so called activators or enhancers. The term "operably linked" as used herein refers to a functional linkage between the promoter sequence and the gene of interest, such that the promoter sequence is able to initiate transcription of the gene of interest.

By way of example, the transgene nucleotide sequence encoding the double-stranded RNA could be placed under the control of an inducible or growth or developmental stage-specific promoter which permits transcription of the dsRNA to be turned on, by the addition of the inducer for an inducible promoter or when the particular stage of growth or development is reached.

In yet other embodiments of the present invention, other promoters useful for the expression of "the second active component," the dsRNA, are used and include, but are not limited to, promoters from an RNA Pol I, an RNA Pol II, an RNA Pol III, T7 RNA polymerase or SP6 RNA polymerase. Vectors comprising these promoters and cells comprising these vectors are described in WO2000/001846 and WO 2001/088151. These promoters are typically used for in vitro-production of dsRNA, which dsRNA is then included in a pesticidal, insecticidal, nematicidal or fungicidal agent, for example, in a pesticidal, insecticidal, nematicidal or fungicidal liquid, spray or powder.

Optionally, one or more transcription termination sequences may also be incorporated in the recombinant construct of the invention. The term "transcription termination sequence" encompasses a control sequence at the end of a transcriptional unit, which signals 3' processing and polyadenylation of a primary transcript and termination of transcription. Vectors comprising these terminators and cells comprising these vectors are described in WO 2001/088151.

Additional regulatory elements, such as transcriptional or translational enhancers, may be incorporated in the expression construct.

Accordingly, the present invention also encompasses a cell comprising any of the nucleotide sequences or recombinant DNA constructs described herein. The invention further encompasses prokaryotic cells (such as, but not limited to, gram-positive and gram-negative bacterial cells) and eukaryotic cells (such as, but not limited to, yeast cells, plant cells, mammalian cells or human cells). Preferably, said cell is a bacterial cell or a plant cell.

Accordingly, the second active component as used herein encompasses a cell (e.g., a bacterial or eukaryotic cell) comprising any of the nucleotide sequences encoding the dsRNA or dsRNA construct as described herein. The present invention also encompasses a cell (e.g., Gram-negative and Gram-positive bacteria, such as, but not limited to, *Escherichia* spp. (e.g. *E. coli*), *Bacillus* spp. (e.g. *B. thuringiensis*), *Rhizobium* spp., *Lactobacilllus* spp., *Lactococcus* spp., etc); or eukaryotic cell such as a yeast cell (e.g. *Saccharomyces* spp.) comprising any of the nucleotide sequences encoding the dsRNA or dsRNA constructs described herein. Preferably, these cells comprise a recombinant construct wherein the nucleotide sequence encoding the dsRNA or dsRNA construct according to the present invention is operably linked to at least one regulatory element as described above.

The bacterial cells as used in the compositions described herein are preferably inactivated when used in an environment where contact with humans or other mammals is likely. Inactivation may be achieved by any means, such as by heat treatment, phenol or formaldehyde treatment for example, or by mechanical treatment.

The compositions of the present invention optionally also can include at least one suitable carrier, excipient or diluent. The composition may contain further components which serve to stabilize the dsRNA and/or prevent degradation of the dsRNA during prolonged storage of the composition. The composition may still further contain components, in addition to the first active component, which enhance or promote uptake of the second active component (e.g., dsRNA) by the pest or pathogen. These may include, for example, chemical agents which generally promote the uptake of RNA into cells, e.g. lipofectamine etc.

The composition containing the two active components may be in any suitable physical form for application to pests or pathogens, to substrates, to cells, or administration to organisms susceptible to infestation or infected by pests or pathogens.

The invention also provides kits that include containers of the two active components described herein. For example, a kit of the invention can include a first container containing an RNA molecule(s) or composition that reduces expression of a selected gene or genes by RNA interference in a cell or organism and a second container containing an amount of one or more sulfated polysaccharides and/or glycosaminoglycans. The amount of the one or more sulfated polysaccharides and/or glycosaminoglycans is sufficient to increase the RNAi effect of the molecule(s) or composition.

Thus it is contemplated that the composition of the invention may be supplied as a "kit-of-parts" comprising the dsRNA in one container and an amount of one or more sulfated polysaccharides and/or glycosaminoglycans in a second container and, optionally, one or more suitable diluents or carriers for the foregoing components in one or more separate containers. In these embodiments the dsRNA may be supplied in a concentrated form, such as a concentrated aqueous solution. It may even be supplied in frozen form or in freeze-dried or lyophilized form. The latter may be more stable for long term storage and may be defrosted and/or reconstituted with a suitable diluent immediately prior to use.

The kit may be supplied with suitable instructions for use. The instructions may be printed on suitable packaging in which the other components are supplied or may be provided as a separate entity, which may be in the form of a sheet or leaflet for example. The instructions may be rolled or folded for example when in a stored state and may then be unrolled and unfolded to direct use of the remaining components of the kit.

The term "pest" as used herein includes a variety of types of pests such as insects. The term "pathogen" as used herein includes a variety of types of pathogens such as nematodes and fungi. The terms "pests" and "pathogens" may imply numerous members from a single species or numerous members from a combination of species comprising insects, nematodes, or fungi.

In preferred, but non-limiting, embodiments of the invention the pest or pathogen is chosen from the group consisting of:

(1) an insect, nematode, or fungus which is a plant pest or pathogen, (2) an insect, nematode, or fungus capable of infesting, infecting or injuring humans and/or animals; and (3) an insect, nematode, or fungus that causes unwanted damage to substrates or materials, such as insects that attack foodstuffs, seeds, wood, paint, plastic, clothing etc.

An insect can be any insect, meaning any organism belonging to the Kingdom Animals, more specific to the Phylum Arthropoda, and to the Class Insecta or the Class Arachnida. The methods of the invention are applicable to all insects and that are susceptible to gene silencing by RNA interference and that are capable of internalizing double-stranded RNA from their immediate environment.

In one embodiment of the invention, the insect may belong to the following orders: Acari, Araneae, Anoplura, Coleoptera, Collembola, Dermaptera, Dictyoptera, Diplura, Diptera, Embioptera, Ephemeroptera, Grylloblatodea, Hemiptera, Homoptera, Hymenoptera, Isoptera, Lepidoptera, Mallophaga, Mecoptera, Neuroptera, Odonata, Orthoptera, Phasmida, Plecoptera, Protura, Psocoptera, Siphonaptera, Siphunculata, Thysanura, Strepsiptera, Thysanoptera, Trichoptera, and Zoraptera.

In preferred, but non-limiting, embodiments of the invention the insect may be one or more of the following non-limiting list:

(1) an insect which is a plant pest, such as, but not limited, to *Nilaparvata* spp. (e.g. *N. lugens* (brown planthopper)); *Laodelphax* spp. (e.g. *L. striatellus* (small brown planthopper)); *Nephotettix* spp. (e.g. *N. virescens* or *N. cincticeps* (green leafhopper), or *N. nigropictus* (rice leafhopper)); *Sogatella* spp. (e.g. *S. furcifera* (white-backed planthopper)); *Blissus* spp. (e.g. *B. leucopterus leucopterus* (chinch bug)); *Scotinophora* spp. (e.g. *S. vermidulate* (rice blackbug)); *Acrosternum* spp. (e.g. *A. hilare* (green stink bug)); *Parnara* spp. (e.g. *P. guttata* (rice skipper)); *Chilo* spp. (e.g. *C. suppressalis* (rice striped stem borer), *C. auricilius* (gold-fringed stem borer), or *C. polychrysus* (dark-headed stem borer)); *Chilotraea* spp. (e.g. *C. polychrysa* (rice stalk borer)); *Sesamia* spp. (e.g. *S. inferens* (pink rice borer)); *Tryporyza* spp. (e.g. *T. innotata* (white rice borer), or *T. incertulas* (yellow rice borer)); *Cnaphalocrocis* spp. (e.g. *C. medinalis* (rice leafroller)); *Agromyza* spp. (e.g. *A. oryzae* (leafminer), or *A. parvicornis* (corn blot leafminer)); *Diatraea* spp. (e.g. *D. saccharalis* (sugarcane borer), or *D. grandiosella* (southwestern corn borer)); *Narnaga* spp. (e.g. *N. aenescens* (green rice caterpillar)); *Xanthodes* spp. (e.g. *X. transversa* (green caterpillar)); *Spodoptera* spp. (e.g. *S. frugiperda* (fall armyworm), *S. exigua* (beet armyworm), *S. litura* (Oriental leafworm), *S. littoralis* (climbing cutworm) or *S. praefica* (western yellowstriped armyworm)); *Mythimna* spp. (e.g. *Mythimna (Pseudaletia) seperata* (armyworm)); *Helicoverpa* spp. (e.g. *H. zea* (corn earworm), *H. armigera*); *Colaspis* spp. (e.g. *C. brunnea* (grape colaspis)); *Lissorhoptrus* spp. (e.g. *L. oryzophilus* (rice water weevil)); *Echinocnemus* spp. (e.g. *E. squamos* (rice plant weevil)); *Diclodispa* spp. (e.g. *D. armigera* (rice hispa)); *Oulema* spp. (e.g. *O. oryzae* (leaf beetle); *Sitophilus* spp. (e.g. *S. oryzae* (rice weevil)); *Pachy*-

*diplosis* spp. (e.g. *P. oryzae* (rice gall midge)); *Hydrellia* spp. (e.g. *H. griseola* (small rice leafminer), or *H. sasakii* (rice stem maggot)); *Chlorops* spp. (e.g. *C. oryzae* (stem maggot)); *Diabrotica* spp. (e.g. *D. virgifera* (western corn rootworm), *D. barberi* (northern corn rootworm), *D. undecimpunctata howardi* (southern corn rootworm), *D. virgifera zeae* (Mexican corn rootworm); *D. balteata* (banded cucumber beetle)); *Ostrinia* spp. (e.g. *O. nubilalis* (European corn borer)); *Agrotis* spp. (e.g. *A. ipsilon* (black cutworm)); *Elasmopalpus* spp. (e.g. *E. lignosellus* (lesser cornstalk borer)); *Melanotus* spp. (wireworms); *Cyclocephala* spp. (e.g. *C. borealis* (northern masked chafer), or *C. immaculata* (southern masked chafer)); *Phaedon* spp. (e.g. *P. cochleariae* (mustard leaf beetle)); *Epilachna* spp. (e.g. *E. varivestis* (Mexican bean beetle)); *Popillia* spp. (e.g. *P. japonica* (Japanese beetle)); *Chaetocnema* spp. (e.g. *C. pulicaria* (corn flea beetle)); *Sphenophorus* spp. (e.g. *S. maidis* (maize billbug)); *Rhopalosiphum* spp. (e.g. *R. maidis* (corn leaf aphid)); *Anuraphis* spp. (e.g. *A. maidiradicis* (corn root aphid)); *Melanoplus* spp. (e.g. *M. femurrubrum* (redlegged grasshopper) *M. differentialis* (differential grasshopper) or *M. sanguinipes* (migratory grasshopper)); *Hylemya* spp. (e.g. *H. platura* (seedcorn maggot)); *Anaphothrips* spp. (e.g. *A. obscrurus* (grass thrips)); *Solenopsis* spp. (e.g. *S. milesta* (thief ant)); or spp. (e.g. *T. urticae* (twospotted spider mite), *T. cinnabarinus* (carmine spider mite); *Helicoverpa* spp. (e.g. *H. zea* (corn earworm), or *H. armigera* (cotton bollworm)); *Pectinophora* spp. (e.g. *P. gossypiella* (pink bollworm)); *Earias* spp. (e.g. *E. vittella* (spotted bollworm)); *Heliothis* spp. (e.g. *H. virescens* (tobacco budworm)); *Anthonomus* spp. (e.g. *A. grandis* (boll weevil)); *Pseudatomoscelis* spp. (e.g. *P. seriatus* (cotton fleahopper)); *Trialeurodes* spp. (e.g. *T. abutiloneus* (banded-winged whitefly) *T. vaporariorum* (greenhouse whitefly)); *Bemisia* spp. (e.g. *B. argentifolii* (silverleaf whitefly)); *Aphis* spp. (e.g. *A. gossypii* (cotton aphid)); *Lygus* spp. (e.g. *L. lineolaris* (tarnished plant bug) or *L. hesperus* (western tarnished plant bug)); *Euschistus* spp. (e.g. *E. conspersus* (consperse stink bug)); *Chlorochroa* spp. (e.g. *C. sayi* (Say stinkbug)); *Nezara* spp. (e.g. *N. viridula* (southern green stinkbug)); *Thrips* spp. (e.g. *T. tabaci* (onion thrips)); *Frankliniella* spp. (e.g. *F. fusca* (tobacco thrips), or *F. occidentalis* (western flower thrips)); *Leptinotarsa* spp. (e.g. *L. decemlineata* (Colorado potato beetle), *L. juncta* (false potato beetle), or *L. texana* (Texan false potato beetle)); *Lema* spp. (e.g. *L. trilineata* (three-lined potato beetle)); *Epitrix* spp. (e.g. *E. cucumeris* (potato flea beetle), *E. hirtipennis* (flea beetle), or *E. tuberis* (tuber flea beetle)); *Epicauta* spp. (e.g. *E. vittata* (striped blister beetle)); *Empoasca* spp. (e.g. *E. fabae* (potato leafhopper)); *Myzus* spp. (e.g. *M. persicae* (green peach aphid)); *Paratrioza* spp. (e.g. *P. cockerelli* (psyllid)); *Conoderus* spp. (e.g. *C. falli* (southern potato wireworm), or *C. vespertinus* (tobacco wireworm)); *Phthorimaea* spp. (e.g. *P. operculella* (potato tuberworm)); *Macrosiphum* spp. (e.g. *M. euphorbiae* (potato aphid)); *Thyanta* spp. (e.g. *T. pallidovirens* (redshouldered stinkbug)); *Phthorimaea* spp. (e.g. *P. operculella* (potato tuberworm)); *Keiferia* spp. (e.g. *K. lycopersicella* (tomato pinworm)); *Limonius* spp. (wireworms); *Manduca* spp. (e.g. *M. sexta* (tobacco hornworm), or *M. quinquemaculata* (tomato hornworm)); *Liriomyza* spp. (e.g. *L. sativae, L. trifolli* or *L. huidobrensis* (leafminer)); *Drosophila* spp. (e.g. *D. simulans, D. yakuba, D. pseudoobscura, D. virilis* or *D. melanogaster* (fruitflies)); *Atherigona* spp. (e.g. *A. soccata* (shoot fly); *Carabus* spp. (e.g. *C. granulatus*); *Chironomus* spp. (e.g. *C. tentanus*); *Ctenocephalides* spp. (e.g. *C. felis* (cat flea)); *Diaprepes* spp. (e.g. *D. abbreviatus* (root weevil)); *Ips* spp. (e.g. *I. pini* (pine engraver)); *Tribolium* spp. (e.g. *T. castaneum* (red floor beetle)); *Glossina* spp. (e.g. *G. morsitans* (tsetse fly)); *Anopheles* spp. (e.g. *A. gambiae* str. PEST (malaria mosquito) or *A. albimanus* (malaria mosquito); *Acyrthosiphon* spp. (e.g. *A. pisum* (pea aphid)); *Apis* spp. (e.g. *A. melifera* (honey bee)); *Homalodisca* spp. (e.g. *H. coagulata* (glassy-winged sharpshooter)); *Aedes* spp. (e.g. *Ae. aegypti* (yellow fever mosquito)); *Bombyx* spp. (e.g. *B. mori* (silkworm)); *Locusta* spp. (e.g. *L. migratoria* (migratory locust)); *Boophilus* spp. (e.g. *B. microplus* (cattle tick))s *Acanthoscurria* spp. (e.g. *A. gomesiana* (red-haired chololate bird eater)); *Diploptera* spp. (e.g. *D. punctata* (pacific beetle cockroach)); *Heliconius* spp. (e.g. *H. erato* (red passion flower butterfly), *H. melpomene* (postman butterfly) or *H. himera*); *Plutella* spp. (e.g. *P. xylostella* (diamontback moth)); *Armigeres* spp. (e.g. *A. subalbatus*); *Culicoides* spp. (e.g. *C. sonorensis* (biting midge)); *Biphyllus* spp. (e.g. *B. lunatus* (skin beetle)); *Mycetophagus* spp (e.g. *M. quadripustulatus*); *Hydropsyche* spp (caddisflies); *Oncometopia* spp. (e.g. *O. nigricans* (sharpshooter)); *Papilio* spp. (e.g. *P. dardanus* (swallowtail butterfly)); *Antheraea* spp. (e.g. *A. yamamai* (japanese oak silkmoth); *Trichoplusia* spp. (e.g. *T. ni* (cabbage looper)); *Callosobruchus* spp. (e.g. *C. maculatus* (cowpea weevil)); *Rhynchosciara* spp. (e.g. *R. Americana* (fungus gnat)); *Sphaerius* spp. (minute bog beatle); *Ixodes* spp. (e.g. *I. scapularis* (black-legged tick)); *Diaphorina* spp. (e.g. *D. citri* (asian citrus psyllid)); *Meladema* spp. (e.g. *M. coriacea* (Black Predacious Diving Beetle); *Rhipicephalus* spp. (e.g. *R. appendiculatus* (brown ear tick)); *Amblyomma* spp. (e.g. *A. americanum* (lone star tick); *Toxoptera* spp. (e.g. *T. citricida* (brown citrus aphid); *Hister* spp.; *Dysdera* spp. (e.g. D. *erythrina* (cell spider)), *Lonomia* spp. (e.g. *L. obliqua* (caterpillar)); and *Culex* spp. (e.g. *C. pipiens* (house mosquito)):

(2) an insect capable of infesting or injuring humans and/or animals such as, but not limited to, those with piercing-sucking or chewing mouthparts or stings, as found in Hemiptera and some Hymenoptera and Diptera such as mosquitos, bees, wasps, lice, fleas and ants as well as members of the Arachnidae, such as ticks and mites;

and (3) an insect that causes unwanted damage to substrates or materials, such as insects that attack foodstuffs, seeds, wood, paint, plastic, clothing etc. Insects or arachnid examples of such pests include household insects, ecto-parasites and insects and/or arachnids relevant for public health and hygiene such as, by way of example and not limitation, flies, spider mites, thrips, ticks, red poultry mite, ants, cockroaches, termites, crickets including house-crickets, silverfish, booklice, beetles, earwigs, mosquitos and fleas.

The term "insect" encompasses insects of all types and at all stages of development, including egg, larval or nymphal, pupal and adult stages.

Additionally, the pathogen may be a fungus or fungi. The fungus or fungi may be one or more of the following not-limiting list:

(1) a fungal cell of, or a cell derived from a plant pathogenic fungus, such as but not limited to *Acremoniella* spp., *Alternaria* spp. (e.g. *Alternaria brassicola* or *Alternaria solani*), *Ascochyta* spp. (e.g. *Ascochyta pisi*), *Botrytis* spp. (e.g. *Botrytis cinerea* or *Botryotinia fuckeliana*), *Cladosporium* spp., *Cercospora* spp. (e.g. *Cercospora kikuchii* or *Cercospora zaea-maydis*), *Cladosporium* spp. (e.g. *Cladosporium fulvum*), *Colletotrichum* spp. (e.g. *Colletotrichum lindemuthianum*), *Curvularia* spp., *Diplodia* spp. (e.g. *Diplodia maydis*), *Erysiphe* spp. (e.g. *Erysiphe graminis* f. sp. *graminis, Erysiphe graminis* f. sp. *hordei* or *Erysiphe pisi*), *Erwinia armylovora, Fusarium* spp. (e.g. *Fusarium nivale, Fusarium sporotrichioides, Fusarium oxysporum, Fusarium graminearum, Fusarium germinearum, Fusarium culmorum,*

*Fusarium solani, Fusarium moniliforme* or *Fusarium roseum*), *Gaeumannomyces* spp. (e.g. *Gaeumannomyces graminis* f. sp. *tritici*), *Gibberella* spp. (e.g. *Gibberella zeae*), *Helminthosporium* spp. (e.g. *Helminthosporium turcicum, Helminthosporium carbonum, Helminthosporium mavdis* or *Helminthosporium sigmoideum*), *Leptosphaeria salvinii, Macrophomina* spp. (e.g. *Macrophomina phaseolina*), *Magnaportha* spp. (e.g. *Magnaporthe oryzae*), *Mycosphaerella* spp., *Nectria* spp. (e.g. *Nectria heamatococca*), *Peronospora* spp. (e.g. *Peronospora manshurica* or *Peronospora tabacina*), *Phoma* spp. (e.g. *Phoma betae*), *Phakopsora* spp. (e.g. *Phakopsora pachyrhizi*), *Phymatotrichum* spp. (e.g. *Phymatotrichum omnivorum*), *Phytophthora* spp. (e.g. *Phytophthora cinnamomi, Phytophthora cactorum, Phytophthora phaseoli, Phytophthora parasitica, Phytophthora citrophthora, Phytophthora megasperma* f. sp. *soiae* or *Phytophthora infestans*), *Plasmopara* spp. (e.g. *Plasmopara viticola*), *Podosphaera* spp. (e.g. *Podosphaera leucotricha*), *Puccinia* spp. (e.g. *Puccinia sorghi, Puccinia striiformis, Puccinia graminis* f. sp. *tritici, Puccinia asparagi, Puccinia recondita* or *Puccinia arachidis*), *Pythium* spp. (e.g. *Pythium aphanidermatum*), *Pyrenophora* spp. (e.g. *Pyrenophora tritici-repentens* or *Pyrenophora teres*), *Pyricularia* spp. (e.g. *Pyricularia oryzae*), *Pythium* spp. (e.g. *Pythium ultimum*), *Rhincosporium secalis, Rhizoctonia* spp. (e.g. *Rhizoctonia solani, Rhizoctonia oryzae* or *Rhizoctonia cerealis*), *Rhizopus* spp. (e.g. *Rhizopus chinensid*), *Scerotium* spp. (e.g. *Scerotium rolfsii*), *Sclerotinia* spp. (e.g. *Sclerotinia sclerotiorum*), *Septoria* spp. (e.g. *Septoria lycopersici, Septoria glycines, Septoria nodorum* or *Septoria tritici*), *Thielaviopsis* spp. (e.g. *Thielaviopsis basicola*), *Tilletia* spp., *Trichoderma* spp. (e.g. *Trichoderma virde*), *Uncinula* spp. (e.g. *Uncinula necator*), *Ustilago maydis* (e.g. corn smut), *Venturia* spp. (e.g. *Venturia inaequalis* or *Venturiapirina*) or *Verticillium* spp. (e.g. *Verticillium dahliae* or *Verticillium albo-atrum*);

(2) a fungal cell of, or a cell derived from a fungus capable of infesting humans and/or animals such as, but not limited to, *Candida* spp., particularly *Candida albicans*; Dermatophytes including *Epidermophyton* spp., *Trichophyton* spp., and *Microsporum* spp. (particularly *Microsporum canis* or *Microsporum gypseum*); *Aspergillus* spp. (particularly *Aspergillus flavus, Aspergillus fumigatus, Aspergillus nidulans, Aspergillus niger* or *Aspergillus terreus*); *Blastomyces dermatitidis; Paracoccidioides brasiliensis; Coccidioides immitis; Cryptococcus neoformans; Histoplasma capsulatum* Var. *capsulatum* or Var. *duboisii; Sporothrix schenckii; Fusarium* spp.; *Scopulariopsis brevicaulis; Trichophyton mentagrophytes, Fonsecaea* spp.; *Penicillium* spp.; or Zygomycetes group of fungi (particularly *Absidia corymbifera, Rhizomucor pusillus* or *Rhizopus arrhizus*);

(3) a fungal cell of, or a cell derived from a fungus that causes unwanted damage to substrates or materials, such as fungi that attack foodstuffs, seeds, wood, paint, plastic, clothing etc. Examples of such fungi are the moulds, including but not limited to *Stachybotrys* spp., *Aspergillus* spp., *Alternaria* spp., *Cladosporium* spp., *Penicillium* spp. or *Phanerochaete chrysosporium*.

Furthermore, the pathogen may be a nematode or nematodes. The nematode or nematodes may be one or more of the following not-limiting list:

(1) a nematode which is a plant pathogenic nematode, such as but not limited to Root Knot Nematodes (*Meloidogyne* spp.) in rice (e.g. *M. incognita, M. javanica* or *M. graminicola*), in soybean (e.g. *M. incognita* or *M. arenaria*), in cotton (e.g. *M. incognita*), in potato (e.g. *M. chitwoodi* or *M. hapla*), in tomato (e.g. *M. chitwoodi*), in tobacco (e.g. *M. incognita, M. javanica* or *M. arenaria*), and in corn (e.g. *M. incognita*); Cyst Nematodes (*Heterodera* spp.) in rice (e.g. *H. oryzae*), in soybean (e.g. *H. glycines*) and in corn (e.g. *H. zeae*); Cyst nematodes (*Globodera* spp.) in potato (e.g. *G. pallida* or *G. rostochiensis*); Reniform Nematodes (*Rotylenchulus* spp.) in cotton (e.g. *R. reniformis*); Root lesion nematodes (*Pratylenchus* spp.) in banana (e.g. *P. coffeae* or *P. goodeyi*); Burrowing Nematodes (*Radopholus* spp.) in banana (e.g. *R. similis*); Other rice damaging nematodes such as rice root nematode (*Hirschmaniella* spp., e.g. *H. oryzae*);

(2) a nematode capable of infesting humans such as, but not limited to: *Enterobius vermicularis*, the pinworm that causes enterobiasis; *Ascaris lumbridoides*, the large intestinal roundworm that causes ascariasis; *Necator* and *Ancylostoma*, two types of hookworms that cause ancylostomiasis; *Trichuris trichiura*, the whipworm that causes trichuriasis; *Strongyloides stercoralis* that causes strongyloidiasis; and *Trichonella spirae* that causes trichinosis; *Brugia malayi* and *Wuchereria bancrofti*, the filarial nematodes associated with the worm infections known as lymphatic filariasis and its gross manifestation, elephantiasis, and *Onchocerca volvulus* that causes river blindness. Transfer of nematodes to humans may also occur through blood-feeding mosquitoes which have fed upon infected animals or humans; or a nematode capable of infesting animals such as, but not limited to: dogs (Hookworms e.g. *Ancylostoma caninum* or *Uncinaria stenocephala*, Ascarids e.g. *Toxocara canis* or *Toxascaris leonina*, or Whipworms e.g. *Trichuris vulpis*), cats (Hookworms e.g. *Ancylostoma tubaeforme*, Ascarids e.g. *Toxocara cati*), fish (herring worms or cod worms e.g. *Anisakid*, or tapeworm e.g. *Diphyllobothrium*), sheep (Wire worms e.g. *Haemonchus contortus*) and cattle (Gastro-intestinal worms e.g. *Ostertagia ostertagi, Cooperia oncophora*);

(3) a nematode that causes unwanted damage to substrates or materials, such as nematodes that attack foodstuffs, seeds, wood, paint, plastic, clothing etc. Examples of such nematodes include but are not limited to *Meloidogyne* spp. (e.g. *M. incognita, M. javanica, M. arenaria, M. graminicola, M. chitwoodi* or *M. hapla*); *Heterodera* spp. (e.g. *H. oryzae, H. glycines, H. zeae* or *H. schachtii*); *Globodera* spp. (e.g. *G. pallida* or *G. rostochiensis*); *Ditylenchus* spp. (e.g. *D. dipsaci, D. destructor* or *D. angustus*); *Belonolaimus* spp.; *Rotylenchulus* spp. (e.g. *R. reniformis*); *Pratylenchus* spp. (e.g. *P. coffeae, P. goodeyi* or *P. zeae*); *Radopholus* spp. (e.g. *R. Similis*); *Hirschmaniella* spp. (e.g. *H. oryzae*); *Aphelenchoides* spp. (e.g. *A. besseyi*); *Criconemoides* spp.; *Longidorus* spp.; *Helicotylenchus* spp.; *Hoplolaimus* spp.; *Xiphinema* spp.; *Paratrichodorus* spp. (e.g. *P. minor*); *Tylenchorhynchus* spp;

and virus transmitting nematodes (e.g. *Longidorus macrosoma*: transmits prunus necrotic ring spot virus, *Xiphinema americanum*: transmits tobacco ring spot virus, *Paratrichadorus teres*: transmits pea early browning virus, or *Trichodorus similis*: transmits tobacco rattle virus).

In one specific embodiment, the composition including the two active components is a pharmaceutical or veterinary composition for treating or preventing insect disease or infections of humans or animals, respectively. Such compositions will comprise at least one double-stranded RNA or RNA construct, or nucleotide sequence or recombinant DNA construct encoding the double-stranded RNA or RNA construct, wherein the double-stranded RNA comprises annealed complementary strands, one of which has a nucleotide sequence which corresponds to a target nucleotide sequence of an insect (target) gene that causes the disease or infection and an amount of one or more sulfated polysaccharides and/or glycosaminoglycans that effectively increases the RNAi effect of the dsRNA, and, optionally, at least one carrier, excipient or diluent suitable for pharmaceutical use.

The composition may be a composition suitable for topical use, such as application on the skin of an animal or human, for example as liquid composition to be applied to the skin as drops, gel, aerosol, or by brushing, or a spray, cream, ointment, etc. for topical application or as transdermal patches.

Other conventional pharmaceutical dosage forms may also be produced, including tablets, capsules, pessaries, transdermal patches, suppositories, etc. The chosen form will depend upon the nature of the target pest or pathogen and hence the nature of the disease it is desired to treat.

In another specific embodiment, the composition including the two active components may be, or be used in, a coating that can be applied to a substrate in order to protect the substrate from infestation by a pest and/or to prevent, arrest or reduce pest growth on the substrate and thereby prevent damage caused by the pest or pathogen. In this embodiment, the composition can be used to protect any substrate or material that is susceptible to infestation by or damage caused by a pest or pathogen, for example foodstuffs and other perishable materials, and substrates such as wood. Houses and other wood products can be destroyed by termites, powder post beetles, and carpenter ants. The subterranean termite and Formosan termite are the most serious pests of houses in the southern United States and tropical regions. Any harvested plant or animal product can be attacked by insects. Flour beetles, grain weevils, meal moths and other stored product pests will feed on stored grain, cereals, pet food, powdered chocolate, and almost everything else in the kitchen pantry that is not protected. Larvae of clothes moths eat clothes made from animal products, such as fur, silk and wool. Larvae of carpet beetles eat both animal and plant products, including leather, fur, cotton, stored grain, and even museum specimens. Book lice and silverfish are pests of libraries. These insects eat the starchy glue in the bindings of books. Other insects that have invaded houses include cockroaches which eat almost anything. Cockroaches are not known to be a specific transmitter of disease, but they contaminate food and have an unpleasant odor. They are very annoying, and many pest control companies are kept busy in attempts to control them. The most common cockroaches in houses, grocery stores, and restaurants include the German cockroach, American cockroach, Oriental cockroach, and brown banded cockroach.

The nature of the excipients and the physical form of the composition may vary depending upon the nature of the substrate that is desired to treat. For example, the composition may be a liquid that is brushed or sprayed onto or imprinted into the material or substrate to be treated, or a coating that is applied to the material or substrate to be treated.

The present invention further encompasses a method for treating and/or preventing pest infestation on a substrate comprising applying an effective amount of any of the compositions described herein to said substrate.

The invention further encompasses a method for treating and/or preventing a disease or condition, comprising administering to a subject in need of such treatment and/or prevention, any of the compositions as herein described, said composition comprising an amount of one or more sulfated polysaccharides and/or glycosaminoglycans that is effective to increase the RNAi effect of dsRNA, and at least one double-stranded RNA or double stranded RNA construct comprising annealed complementary strands, one of which has a nucleotide sequence which is complementary to at least part of a nucleotide sequence of a pest or pathogen (target) gene that causes the insect disease or condition.

Therapeutic use of the compositions described herein includes administering to an individual in a effective dose sufficient to treat a disorder by knocking down expression of a (target) gene. The effective amount may vary according to a variety of factors such as the gene or genes targeted, the particular composition administered, the individual's condition, weight, sex and age. Other factors include the route of administration. Pharmaceutical compositions may be administered to the individual by a variety of routes such as by topical, parenteral, enteral, transdermal, cutaneous, subcutaneous, intravenous, intraperitoneal, intramuscular or oral routes. In addition, co-administration or sequential administration of the two active components or other agents may be desirable.

In another embodiment of the invention the compositions are used as a pesticide, insecticide, nematicide or fungicide for a plant or for propagation or reproductive material of a plant, such as on seeds. As an example, the composition can be used as a pesticide, insecticide, nematicide or fungicide by spraying or applying it on plant tissue or spraying or mixing it on the soil before or after emergence of the plantlets.

In yet another embodiment, the present invention provides a method for treating and/or preventing insect growth and/or insect infestation of a plant or propagation or reproductive material of a plant, comprising applying an effective amount of any of the compositions herein described to a plant or to propagation or reproductive material of a plant.

EXAMPLES

The following examples illustrate the present invention in more detail. These examples are meant to be exemplary and not as limitations of the present invention. A range of compounds were tested for enhanced RNAi-induced lethality with each compound coadministered with the target double-stranded RNA in feeding bioassays against larvae of the Colorado potato beetle (*Leptinotarsa decemlineata*), the mustard leaf beetle (*Phaedon cochleariae*) and the nematode worm *Caenorhabditis elegans*. The sulfated polysaccharide, dextran sulfate, substantially increased the RNAi-induced lethality of target dsRNA when the two components were ingested. Ingestion of target dsRNA in the presence of the glycosaminoglycan, heparin, also increased insect mortality when compared to target dsRNA alone.

Example 1

The Effects of Dextran Sulfate (±8 kDa) at Different Concentrations

In a Colorado potato beetle (CPB) larvae bioassay, target Ld105 dsRNA (SEQ ID NO:1) was tested at one amount (50 ng) in the presence of dextran sulfate (average Mw±8 kDa; Sigma cat. no. D4911) at different amounts ranging from 50 ng to 50 µg per larvae. The bioassay was typically performed in an 48-well-plate containing 500 µl of artificial diet per well. Thirty µl of test solution consisting of 5 µl Ld105 (SEQ ID NO 1) dsRNA (starting concentration 10 ng/µl) and 25 µl of dextran sulfate (of varying concentrations in Milli-Q water) was applied topically to the diet and the diet left to dry for about two hours in the laminar flow at room temperature. One $2^{nd}$ stage CPB larva was placed in each well. Per treatment, 24 insects were tested. The plates were incubated in the insect rearing chamber at 25° C. and ±50% RH, with a photoperiod of 16 hours light/8 hours dark. Mortality was scored over the course of the experiment. The Kaplan-Meier estimator was used to plot the survival curves and the survival curves were compared using the logrank $\chi^2$ test.

The time-to-kill, i.e. the time it takes to reach a certain mortality number in each treatment, was reduced when target dsRNA was accompanied with dextran sulfate, as shown in FIG. 1. In this bioassay, at day 7 (i.e. 7 days post infestation on artificial diet), approximately 60% of larvae had been killed in the treatments of dsRNA with dextran sulfate at 5 or 50 µg, whereas approx. 30% (i.e. half) of larvae died on diet containing target dsRNA alone. In this bioassay, it took at least an extra 5 days for the number of dead CPB larvae to reach 60% in the treatment of dsRNA alone; at this time, day 12 onwards, more than 90% of CPB larvae were killed in the treatments of dsRNA with an amount of 5 or 50 µg dextran sulfate. Very little or no toxicity was associated with dextran sulfate alone.

In this bioassay, overall potency was increased. Over the course of the whole bioassay, the percentage of CPB larval survivors was substantially lower where these insects have been feeding on a diet containing target dsRNA with dextran sulfate at the two highest concentrations than with those on a diet with target dsRNA alone ($\chi^2=8.558$ and P-value=0.0034 for 5 µg dextran sulfate supplement, and $\chi^2=8.764$ and P-value=0.0031 for 50 µg dextran sulfate supplement).

Thus, it was shown that the sulfated polysaccharide, dextran sulfate, substantially increased the RNAi-induced lethality of target dsRNA when the two components were ingested.

Example 2

The Effects of Fucoidan at Different Concentrations

In a CPB bioassay (set-up described in Example 1), target Ld105 dsRNA (SEQ ID NO:1) was tested at one quantity (50 ng) in the presence of fucoidan (average Mw±20 kDa; Sigma cat. no. F5631) at different amounts ranging from 50 ng to 50 µg per larva.

The time-to-kill was observed to be reduced with target Ld105 dsRNA in the presence of fucoidan when compared to target dsRNA alone, as is shown in FIG. 2. In this bioassay, at day 7, approx. 70% of larvae were killed in the treatment of dsRNA with 50 µg fucoidan whereas approx. 45% of larvae died on diet containing target dsRNA alone. Very little or no toxicity was associated with fucoidan alone.

Example 3

The Effects of Polyinosine at Different Concentrations

In a CPB bioassay (set-up described in Example 1 but with polyinosine dissolved in 0.9 M NaCl), target Ld105 dsRNA (SEQ ID NO:1) was tested at one quantity (50 ng) in the presence of the nucleotide polyinosine (poly I; Sigma cat. no. P4154) at different amounts ranging from 50 ng to 50 µg per larva. Very little or no toxicity was associated with poly I alone.

No significant effects (P-value>0.05) were obtained, as is shown in FIG. 3.

Example 4

The Effects of Different Concentrations of Target dsRNA and One Concentration of Dextran Sulfate (±8 kDa)

In a CPB bioassay (set-up described in Example 1), target Ld105 dsRNA (SEQ ID NO:1) was tested at different amounts ranging from 1 pg to 1 µg in the presence of 50 µg dextran sulfate per larva.

The time-to-kill was reduced for treatments with dsRNA at 1 µg or 100 ng and 50 µg dextran sulfate when compared to target dsRNA alone treatment, as is shown in FIG. 4. At day 7, CPB mortality with dsRNA alone was 29 and 38% for 1 µg and 100 ng of Ld105 dsRNA, respectively, whereas in the presence of dextran sulfate the number of dead larvae had approx. doubled to 79 and 63%, respectively. Very little or no toxicity was associated with dextran sulfate alone.

Over the course of the bioassay, the CPB survival numbers of the 1 µg and 100 ng target dsRNA with dextran sulfate treatments were significantly reduced when compared to target dsRNA alone at the same quantaties ($\chi^2=12.56$ and P-value=0.0004, and $\mu^2=5.671$ and P-value=0.0173, respectively).

Example 5

The Effects of Dextran Sulfate (±1400 kDa) at Different Concentrations

In a CPB bioassay (set-up described in Example 1), target Ld105 dsRNA (SEQ ID NO:1) was tested at one quantity (50 ng) in the presence of dextran sulfate (average Mw±1400 kDa; MP Biomedicals cat. no. 193992) at different amounts ranging from 50 ng to 50 µg per larva.

The time-to-kill was reduced for treatment dsRNA with 50 µg dextran sulfate, as is shown in FIG. 5. In this bioassay, at day seven, 75% of larvae had been killed in the treatments of dsRNA with dextran sulfate at 50 µg, whereas 33% of larvae died on diet containing target dsRNA alone. Very little or no toxicity was associated with dextran sulfate alone.

In this bioassay, overall potency was increased. Over the course of the whole bioassay, the percentage of CPB larval survivors was substantially lower where these insects have been feeding on a diet containing target dsRNA with dextran sulfate at the highest concentration (i.e. 50 µg) than with those on a diet with target dsRNA alone ($\chi^2=6.680$ and P-value=0.0097). Lower amounts (i.e. 5 µg, 500 ng or 50 ng) of dextran sulfate with target dsRNA did not significantly increase CPB larval mortality when compared to target dsRNA alone (P-value>0.05).

Example 6

The Effects of Heparin at Different Concentrations

In a CPB bioassay (set-up described in Example 1), target Ld105 dsRNA (SEQ ID NO: 1) was tested at one quantity (50 ng) in the presence of heparin (MP Biomedicals cat. no. 194114) at different amounts ranging from 50 ng to 50 µg per larva.

The time-to-kill was reduced for treatment dsRNA with 50 µg heparin, as is shown in FIG. 6. In this bioassay, at day seven, approx. 21% of larvae had been killed in the treatments of dsRNA with heparin at 50 µg, whereas aprox. 8% of larvae died on diet containing target dsRNA alone. Dextran sulfate at 50 µg per larva with target dsRNA was included in this bioassay and resulted in 50% mortality at day 7. Very little or no toxicity was associated with heparin and dextran sulfate (see Example 1) alone.

Over the course of the whole bioassay, the percentage of CPB larval survivors was substantially lower where these insects have been feeding on a diet containing target dsRNA with heparin at the highest concentration (i.e. 50 µg) than with those on a diet with target dsRNA alone ($\chi^2=4.995$ and P-value=0.026). Lower concentrations (i.e. 5 µg, 500 ng or 50 ng) of heparin with target dsRNA did not significantly increase CPB larval mortality when compared to target dsRNA alone (P-value>0.05). Target dsRNA with 50 μg dextran sulfate was more toxic than Ld105 dsRNA alone ($\chi^2$=22.24 and P-value<0.0001) or with the highest concentration of heparin tested ($\chi^2$=8.566 and P-value=0.0034).

Thus, it was shown that the sulfated glycosaminoglycan, heparin, substantially increased the RNAi-induced lethality of target dsRNA when the two components were ingested.

Example 7

The Effects of Chondroitin Sulfate and Hyaluronic Acid at One Concentration

In a CPB bioassay (set-up described in Example 1), target Ld105 dsRNA (SEQ ID NO:1) was tested at one quantity (50 ng per larva) in the presence of 50 μg chondroitin sulfate (Sigma cat. no. C3788) or hyaluronic acid (Sigma cat. no. 53747).

A strong tendency for a reduction in time-to-kill was observed (FIG. 7) with target Ld105 dsRNA in the presence of either chondroitin sulfate or hyaluronic acid when compared to Ld105 dsRNA alone.

Example 8

The Effects of Dextran Sulfate (±8 kDa) on Bacterial-Expressed dsRNA Activity

Heat-killed recombinant *Escherichia coli* with expressed double-stranded RNA of target Ld105 (designated as pGBNJ003) or control (designated as pGN29) was tested at different amounts in the presence of 50 μg dextran sulfate (Mw±8 kDa) in a CPB bioassay (set-up described in Example 1). Preparation of the recombinant bacteria is described in the international publication WO 2007/080127 (see pages 55-56).

The time-to-kill was substantially reduced for each treatment with pGBNJ003 plus dextran sulfate when compared to pGBNJ003 only treatments (FIG. 8). For example, at day 10, dextran sulfate increased CPB larval mortality from 31% to 88% for pGBNJ003 at 0.25 U, from 62% to 88% for pGBNJ003 at 008 U, and from 13% to 56% for pGBNJ003 at 0.027 U (where 1 unit (U) corresponds to the amount of bacteria present in 1 mL culture with an OD600 nm value of 1 prior to heat-inactivation).

Over the course of the bioassay, the CPB survival numbers in all treatments of pGBNJ003 with dextran sulfate were significantly reduced when compared to pGBNJ003 alone at the respective concentrations ($\chi^2$=10.93 and P-value=0.0009 for 0.25 U, $\chi^2$=7.524 and P-value=0.0061 for 0.08 U, $\chi^2$=11.33 and P-value=0.0008 for 0.027 U). No toxicity was observed with pGN29 controls in the absence or presence of dextran sulfate.

Thus, it was demonstrated that dextran sulfate substantially increased RNAi-induced lethality of bacterial-expressed target dsRNA when both components were ingested by the CPB larvae.

Example 9

The Effects of Dextran Sulfate (±8 kDa) with dsRNAs from Different Targets

In one CPB bioassay (set-up described in Example 1), different target dsRNAs (SEQ ID NO:1, 2, 3, 4; Ld105 dsRNA=SEQ ID NO:1, Ld013=SEQ ID NO: 2, Ld009=SEQ ID NO: 3 and Ld248=SEQ ID NO: 4) were tested at one quantity (100 ng) in the presence of dextran sulfate (50 μg).

Over the course of the bioassay, the percentages of CPB larval survivors were substantially lower where these insects have been feeding on a diet containing any of the target dsRNAs in combination with dextran sulfate than those on a diet with the respective target dRNAs alone (Ld009: $\chi^2$=15.70 and P-value<0.0001; Ld013: $\chi^2$=14.50 and P-value=0.0001; Ld105: $\chi^2$=20.57 and P-value<0.0001; Ld248: $\chi^2$=13.45 and P-value=0.0002), as is shown in FIG. 9. The effects observed with Ld105 dsRNA plus dextran sulfate in this assay were comparable to those observed in another assay shown in FIG. 4 (of Example 4); the target dsRNA alone treatment responses were different between the two assays as a consequence of variabilities between assays.

Thus, it was demonstrated that the sulfated polysaccharide, dextran sulfate, substantially increased the RNAi-induced lethality of different target dsRNAs when the two components were ingested.

Example 10

The Effects of Dextran Sulfate (±8 kDa) Using an Alternative Bioassay System An alternative bioassay was used using potato leaf discs rather than artificial diet as food source for CPB. Discs of approximately 0.9 cm in diameter (or 0.64 $cm^2$) were cut out off leaves of 4- to 6-week-old potato plants using a suitably sized cork borer. Treated leaf discs were prepared by applying 2 μl of a solution comprising 100 ng target Ld105 dsRNA (SEQ ID NO:1) and 50 μg dextran sulfate on the adaxial leaf surface. The leaf discs were allowed to dry and placed individually in 24 wells of a 48-well multiwell plate. A single second-larval stage CPB was placed into each well and the plate covered with a plastic lid. Twenty-four larvae were tested per treatment. The plates containing the larvae on leaf discs were kept in the insect rearing chamber as described in Example 1. After 24 hours, the larvae were transferred to fresh, untreated leaf discs and placed in the chamber for a further 24 hours. This was repeated once after which the CPB larvae were transferred on to artificial diet where they were kept until the end of the bioassay.

The time-to-kill was reduced for treatments with dsRNA at 100 ng or 10 ng and 50 μg dextran sulfate when compared to target dsRNA alone treatment, as is shown in FIG. 10. At day 8, CPB mortality with dsRNA alone was 33 and 21% for 100 and 10 ng of Ld105 dsRNA, respectively, whereas in the presence of dextran sulfate the number of dead larvae had approx. doubled to 71 and 58%, respectively. Very little toxicity was associated with dextran sulfate alone.

Over the course of the bioassay, the CPB survival numbers of the 100 and 10 ng target dsRNA with dextran sulfate treatments were significantly reduced when compared to target dsRNA alone at the same concentrations ($\chi^2$=5.071 and P-value=0.0243, and $\chi^2$=15.42 and P-value<0.0001, respectively).

Example 11

Priming Insects with Dextran Sulfate for Increased RNAi-Induced Killing

In one CPB bioassay, target Ld105 dsRNA (SEQ ID NO:1) was tested at one quantity (1 μg) following a short exposure to dextran sulfate only. The bioassay set-up was similar to that described in Example 1, except that the larvae were first fed diet with topically applied dextran sulfate (DS; 50 μg), or water, for two full days before transferring them to fresh diet with topically applied Ld105 dsRNA, dextran sulfate or water only, for the remainder of the assay.

The time-to-kill was reduced for treatment with dsRNA after first fed with dextran sulfate (i.e. DS/dsRNA), as is shown in FIG. 11. In this bioassay, at day eight, approx. 58% of larvae had been killed in the DS/dsRNA treatment, whereas approx. 38% of larvae died in the water/dsRNA treatment. Very little or no toxicity was observed in the water/water and DS/DS treatments.

Over the course of the whole bioassay, there was a tendency towards a lower percentage of CPB larval survivors in the DS/dsRNA treatment when compared to the water/dsRNA treatment.

Example 12

The Effects of Dextran Sulfate (±8 kDa) on RNAi-Induced Killing of the Mustard Leaf Beetle To test the effects of dextran sulfate on the RNAi-induced killing of another insect species, namely, the mustard leaf beetle (*Phaedon cochleariae*; MLB), a leaf-disc assay was used. Discs of approximately 1.1 cm in diameter (or 0.95 $cm^2$) were cut out off leaves of 4- to 6-week-old oilseed rape plants using a suitably sized cork borer. Treated leaf discs were prepared by applying 25 μl of a 0.05% Triton X-100 solution comprising 50 ng target Pc105 dsRNA (SEQ ID NO: 5) and 50 ng dextran sulfate on the adaxial leaf surface. The droplet was spread over the leaf disc surface and the leaf discs were allowed to dry. The leaf discs were placed individually in wells of a 128-well multiwell plate (CD-International) containing 1 ml of gellified 2% agar. A single second-larval stage MLB was placed into each well and the plate covered with a plastic lid. Thirty larvae were tested per treatment. The plates containing the larvae on leaf discs were kept in the insect rearing chamber as described for CPB in Example 1. The larvae were allowed to consume the whole treated leaf disc before transferring them onto fresh untreated leaf discs. Refreshing of the leaf material was repeated until the end of the bioassay.

The time-to-kill was reduced for treatment dsRNA with dextran sulfate, as is shown in FIG. 12. In this bioassay, at day four, approx. 90% of larvae had been killed in the treatment dsRNA with dextran sulfate, whereas approx. 60% of larvae died on leaf discs treated with target dsRNA alone.

Over the course of the whole bioassay, the percentage of MLB larval survivors was substantially lower where these insects have been feeding on leaf discs treated with target dsRNA plus dextran sulfate than those on leaf discs with target dsRNA alone ($\chi^2$=7.995 and P-value=0.0047).

Thus, it was shown that dextran sulfate substantially increased the RNAi-induced lethality of target dsRNA when the two components were ingested by an insect species other than the Colorado potato beetle, namely, the mustard leaf beetle.

Example 13

The Effects of Dextran Sulfate (±8 kDa) on RNAi-Induced Phenotype of a Non-Insect Species, the Nematode *Caenorhabditis elegans*

The effects of dextran sulfate on the RNAi-induced phenotypes of a non-insect species, namely, the nematode *Caenorhabditis elegans*, were tested in a soaking assay. Wild-type worms were chunked from a stock plate and adults were bleached to obtain a well-staged population. The assay was set up in a V-shaped 96-well plate, with each well containing 20 μl of solution comprising 50 ng/μl target rps-14 dsRNA (SEQ ID NO:6), various concentrations of dextran sulfate (0 mg/ml, 0.25 mg/ml, 0.50 mg/ml and 1 mg/ml) and 50 first-larval stage nematodes. Each treatment was performed in triplicate. The plate containing the worms was incubated at 25° C. for overnight soaking. After 17 hours, the worms were transferred to 3.5 cm agar-plates seeded with OP50 *E. coli* and incubated at 20° C. for a further 2 days. After this growing period, the assay was assessed by counting the different life stages for all treatments.

Treatments with 50 ng/μl dsRNA and dextran sulfate resulted in a reduction in numbers of adults and L4 stage larvae, while the number of L3 stage and dead larvae increased when compared to target dsRNA alone treatment, as shown in FIG. 13. The number of adults and L4 stage larvae decreased from 63% and 19%, respectively, to 48% and 11%, respectively, in the dsRNA plus 1 mg/ml dextran sulfate treatment. Number of L3 stage and dead larvae increased from 11% and 7%, respectively, to 28% and 13%, respectively, in the dsRNA plus 1 mg/ml dextran sulfate treatment. No toxicity was associated with dextran sulfate alone (data not shown).

In this bioassay, an increase in developmental delay of the *C. elegans* population was observed when worms were soaked in target dsRNA in the presence of dextran sulfate compared to the target dsRNA alone treatment.

Those skilled in the art will recognize, or be able to ascertain using no more than routine experimentation, many equivalents to the specific embodiments of the invention described herein. Such equivalents are intended to be encompassed by the following claims.

All references disclosed herein are incorporated by reference in their entirety for the purposes indicated herein.

We claim:

1. A method for protecting plants or foodstuffs from pest infestation or pathogen infection comprising contacting the plant or the soil on which the plant is rooted, or foodstuff with
   (1) a first composition comprising an amount of one or more of dextran sulfate, fucoidan, heparin, chondroitin sulfate and hyaluronic acid that is effective to enhance the RNAi effect of a double-stranded RNA molecule(s) and
   (2) a second composition comprising a double-stranded RNA molecule(s) that reduces expression of a selected gene or genes from the pest or pathogen by RNA interference.

2. The method of claim 1, wherein the plant or the soil on which the plant is rooted, or foodstuff is contacted with the first composition
   (i) before or after contacting the plant or the soil on which the plant is rooted, or foodstuff with the second composition,
   (ii) simultaneously with contacting the plant or the soil on which the plant is rooted, or foodstuff with the second composition, or
   (iii) before, simultaneously with and/or after contacting the plant or the soil on which the plant is rooted, or foodstuff with the second composition.

3. The method of any of claim 1 or 2, wherein the contacting comprises applying or spraying the second composition and the first composition onto the plant or foodstuff.

4. A method for treating a plant infection by a pathogen or plant infestation by a pest comprising contacting the plant or the soil in which the plant is rooted with
   (1) a first composition comprising an amount of one or more of dextran sulfate, fucoidan, heparin, chondroitin sulfate and hyaluronic acid that is effective to enhance the RNAi effect of a double-stranded RNA molecule(s) and
   (2) a second composition comprising a double-stranded RNA molecule(s) that reduces expression of a selected gene or genes from the pest or pathogen by RNA interference.

5. A method for increasing crop yield or reducing a decline in crop yield that results from pest infestation and/or pathogen infection comprising contacting the plant or the soil wherein the plant is rooted with (1) a first composition comprising an amount of one or more of dextran sulfate, fucoidan, heparin, chondroitin sulfate and hyaluronic acid that is effective to enhance the RNAi effect of a double-stranded RNA molecule(s) and (2) a second composition comprising a double-stranded RNA molecule(s) that reduces expression of a selected gene or genes from the pest or pathogen by RNA interference.

6. The method of any of claim 4 or 5, wherein the plant or the soil on which the plant is rooted is contacted with the first composition
   (i) before or after contacting the plant or the soil on which the plant is rooted with the second composition,
   (ii) simultaneously with contacting the plant or the soil on which the plant is rooted with the second composition, or
   (iii) before, simultaneously with and/or after contacting the plant or the soil on which the plant is rooted with the second composition.

7. The method of any of claim 4 or 5, wherein the contacting comprises applying or spraying the second composition and the first composition onto the plant or onto the soil wherein the plant is rooted.

* * * * *